(12) United States Patent
Ali et al.

(10) Patent No.: US 8,648,058 B2
(45) Date of Patent: Feb. 11, 2014

(54) DIAZENIUMDIOLATE CYCLOPENTYL DERIVATIVES

(75) Inventors: Amjad Ali, Freehold, NJ (US); Michael Man-Chu Lo, Edison, NJ (US); Edward Metzger, Somerset, NJ (US); Lin Yan, Brunswick, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/577,797

(22) PCT Filed: Feb. 10, 2011

(86) PCT No.: PCT/US2011/024275
§ 371 (c)(1),
(2), (4) Date: Aug. 8, 2012

(87) PCT Pub. No.: WO2011/103012
PCT Pub. Date: Aug. 25, 2011

(65) Prior Publication Data
US 2013/0053352 A1    Feb. 28, 2013

Related U.S. Application Data

(60) Provisional application No. 61/303,927, filed on Feb. 12, 2010.

(51) Int. Cl.
*A61K 31/655* (2006.01)
*C07C 245/24* (2006.01)

(52) U.S. Cl.
USPC .......................................... 514/151; 534/552

(58) Field of Classification Search
None
See application file for complete search history.

(56) References Cited

U.S. PATENT DOCUMENTS

| 5,366,997 A | 11/1994 | Keefer et al. |
| 2003/0147845 A1 | 8/2003 | Saavedra et al. |

FOREIGN PATENT DOCUMENTS

| WO | WO 2009/070241 | 6/2009 |
| WO | WO 2009/094242 | 7/2009 |

OTHER PUBLICATIONS

Supplementary European Search Report of EP 11 74 2769, dated Jul 13, 20132; 4 pages.
International Search Report for corresponding application PCT/US2011/24275 dated Apr. 15, 2011.

*Primary Examiner* — Michael Barker
(74) *Attorney, Agent, or Firm* — Nicole M. Beeler; Catherine D. Fitch

(57) ABSTRACT

A compound of formula I,

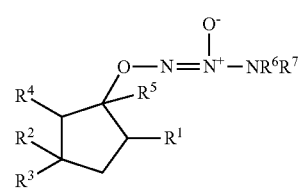

wherein R1-R7 are defined herein, or stereoisomers therof, or pharmaceutically acceptable salts thereof, or pharmaceutically acceptable salts of stereoisomers thereof, and methods of using these compounds for treating hypertension.

18 Claims, 13 Drawing Sheets

DIAZENIUMDIOLATE CYCLOPENTYL DERIVATIVES

BACKGROUND OF THE INVENTION

Figure 1A:
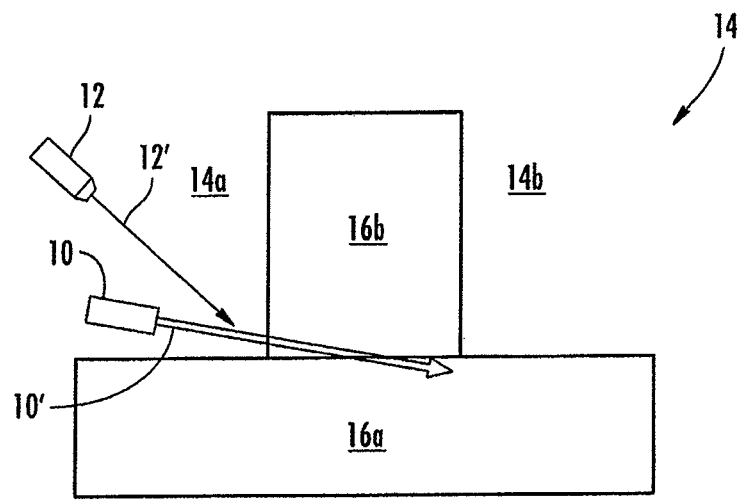

WO09103875 describes diazeniumdiolate dihydro indole derivatives of a specified formula for treating hypertension and cardiovascular disease. WO07144512 describes diazeniumdiolate tetrazole-biphenyl derivatives of a specified formula for treating hypertension and cardiovascular disease. US 2005137191 describes nitrate ester compounds, e.g., 1,2-dichloro-4-(2-methyl-butyldisulfanyl)-benzene, useful for preventing or mitigating tissue and/or cellular damage associated with aging, septic shock, ulcers, gastritis, ulcerative colitis and Crohn's disease. US 2005065194 describes use of an endothelial gene differentiation receptor modulator such as 1-(2-ethoxyphenyl)-3-(hydroxyphenylamino)-pyrrolidine-2,5-dione, to modulate receptor-mediated biological activity such as cell proliferation stimulated by lysophosphatidic acid leading to ovarian cancer and other forms of cancer, and to treat conditions such as cancer, cardiovascular disease, ischemia, and atherosclerosis. WO 9746521 describes aliphatic nitrate esters useful for treating neurological conditions, especially Parkinson's, Alzheimer's and Huntington's disease.

The present invention relates to novel diazeniumdiolate cycloalkane derivatives, useful as antihypertensive agents.

SUMMARY OF THE INVENTION

The present invention includes diazeniumdiolate cycloalkane derivatives, including various pharmaceutically acceptable salts and hydrates of these forms, and pharmaceutical formulations for controlled and sustained delivery of these forms to a patient.

The invention also includes a method for treating hypertension, Pulmonary Arterial Hypertension (PAH), congestive heart failure, conditions resulting from excessive water retention, cardiovascular disease, diabetes, oxidative stress, endothelial dysfunction, cirrhosis, pre-eclampsia, osteoporosis or nephropathy, comprising administering a compounds of the invention to a patient having such a condition, or being at risk to having such condition.

DETAILED DESCRIPTION OF THE INVENTION AND PREFERRED EMBODIMENTS

The invention is a compound of formula I:

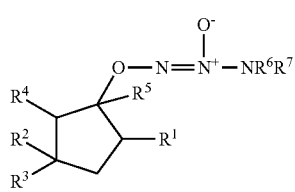

I or a pharmaceutically acceptable salt thereof, wherein
$R^1$ is hydrogen, —OH, —O—$C_{1-6}$ alkyl, =O, or halogen;
$R^2$ is
  hydrogen,
  —C(O)O$R^8$,
  —$C_6H_5$C(O)O$R^8$,
  —(CH$_2$)$_{1-2}$OH,
  —C$R^9R^{10}$OH,
  —C(O)O(CH$_2$)$_{0-2}$ aryl,
  —C(O)N$R^9R^{10}$,
  —C(O)SO$_2$N$R^9R^{10}$,
  —$C_6H_5$O$R^9$,
  —W—C(O)O$R^8$,
  —W—O$R^9$,
  —Y, or
  —P(O)(O$R^9$)(O$R^{10}$);
$R^3$ is hydrogen or —$C_{1-6}$ alkyl;
$R^4$ is hydrogen, —OH, or —C(O)O$R^9$;
$R^5$ is hydrogen or deuterium;
$R^6$ and $R^7$ are independently —$C_{1-6}$ alkyl, fluoro-substituted-$C_{1-6}$ alkyl, deutero-substituted —$C_{1-6}$ alkyl or —(CH$_2$)$_{1-2}$$R^{11}$, wherein any carbon atom of the fluoro-substituted-$C_{1-6}$ alkyl is mono- or di-substituted with fluoro, and any carbon atom of the deutero-substituted —$C_{1-6}$ alkyl is mono- or di-substituted with fluoro;
$R^8$, in each instance in which it occurs, is independently hydrogen, —$C_{1-6}$ alkyl, or —(CH$_2$)$_2$N$^+$(CH$_3$)$_3$;
$R^9$ and $R^{10}$, in each instance in which they occur, are independently —$C_{1-6}$ alkyl;
$R^{11}$ is —OH, —O—$C_{1-6}$ alkyl, —OCD3, —OC(O)O$C_{1-6}$ alkyl, —NH$_2$, —$C_6H_5$, —N3, or W;
W is an unsubstituted 5- or 6-membered heteroaryl ring having 1, 2, or 3 nitrogen atoms, or a substituted 5- or 6-membered heteroaryl ring having 1, 2, or 3 nitrogen atoms that is mono- or di-substituted at any carbon atom with a group selected from $R^6$ and $R^7$;
Y is a 5- or 6-membered heterocyclic ring having 1, 2, 3 or 4 heteroatoms which are independently N, O or S,
and stereoisomers thereof, and pharmaceutically acceptable salts thereof, and pharmaceutically acceptable salts of stereoisomers thereof.

In one embodiment of the invention, the compound has the formula Ia:

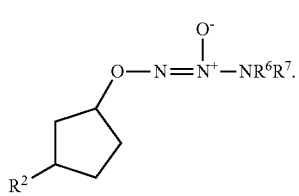

Ia

In another embodiment of the invention, $R^1$ is hydrogen, —OH, —OCH$_3$, =O, or F.

In another embodiment of the invention, $R^2$ is
  —C(O)OR$S$,
  —$C_6H_5$C(O)O$R^S$,
  —(CH$_2$)$_{1-2}$OH,
  —C(O)O(CH$_2$)$_{0-2}$ aryl,
  —$C_6H_5$O$R^9$, or
  —P(O)(O$R^9$)(O$R^{10}$).

In another embodiment of the invention, $R^2$ is
  —C(O)OH,
  —C(O)OCH$_3$,
  —C(O)OCH$_2$CH$_3$,
  —C(O)OC$_6H_5$,
  —C(O)OCH$_2$CH$_2$N(CH$_3$)$_3$,
  —$C_6H_5$C(O)OCH$_2$CH$_3$,
  —$C_6H_5$C(O)OH,
  —CH$_2$OH,
  —C(O)OCH$_2C_6H_5$,
  —$C_6H_5$OCH$_3$, or
  —P(O)(OCH$_2$CH$_3$)$_2$.

In another embodiment of the invention, $R^3$ is hydrogen or —CH$_3$.

In another embodiment of the invention, $R^3$ is hydrogen.

In another embodiment of the invention, $R^4$ is hydrogen, —OH, or —C(O)OCH$_2$CH$_3$.

In another embodiment of the invention, $R^4$ is hydrogen.

In another embodiment of the invention, $R^5$ is hydrogen.

In another embodiment of the invention, $R^6$ is

—CH$_3$,
—CH(CH$_3$)$_2$,
—CH$_2$CH$_3$,
—(CH$_2$)$_3$CH$_3$,
—(CH$_2$)$_2$CH(CH$_3$)$_2$,
—(CH$_2$)$_2$OH,
—(CH$_2$)$_2$OCH$_3$,
—(CH$_2$)$_2$OCD$_3$,
—(CH$_2$)$_2$OC(O)OC(CH$_3$)$_3$,
—NH$_2$
—CH$_2$CH$_2$CH$_3$,
—CH$_2$CH$_2$N$^+{}_3$, or

—(CH$_2$)$_2$—[triazole ring].

In another embodiment of the invention, $R^7$ is —C(CH$_3$)$_3$ or —CH$_2$C$_6$H$_5$.

In another embodiment of the invention, $R^7$ is —C(CH$_3$)$_3$.

In another embodiment of the invention, the compound is (1R,3R)-3-({[(1Z)-2-tert-butyl-2-ethyl-1-oxido-1λ$^5$-diazan-1-ylidene]amino}oxy)cyclopentanecarboxylic acid (Ex. 1)

ethyl (1R,3R)-3-({[(1Z)-2-tert-butyl-2-ethyl-1-oxido-1λ$^5$-diazan-1-ylidene]amino}oxy)cyclopentanecarboxylate (Ex. 1, step C)

(1S,3S)-3-({[(1Z)-2-tert-butyl-2-ethyl-1-oxido-1λ$^5$-diazan-1-ylidene]amino}oxy)cyclopentanecarboxylic acid (Ex. 2)

(1R,3R)-3-({[(1Z)-2-tert-butyl-2-methyl-1-oxido-1λ$^5$-diazan-1-ylidene]amino}oxy)cyclopentanecarboxylic acid (Ex. 3)

(1S,3S)-3-({[(Z)-2-tert-butyl-2-methyl-1-oxido-1λ$^5$-diazan-1-ylidene]amino)}oxy)cyclopentanecarboxylic acid (Ex. 4)

(1R,3R)-3-({[(1Z)-2-tert-butyl-2-(2-methoxyethyl)-1-oxido-1λ$^5$-diazan-1-ylidene]amino}oxy)cyclopentanecarboxylic acid (Ex. 5)

2-{tert-butyl[(Z)-{[(1R,3R)-3-(4-methoxyphenyl)cyclopentyl]oxy}-NNO-azoxy]amino)}ethanol (Ex. 5, step D)

N-(2-methoxyethyl)-N—[(Z)-{[(1R,3R)-3-(4-methoxyphenyl)cyclopentyl]oxy}-NNO-azoxy]-2-methylpropan-2-amine (Ex. 5, step E)

(1R,3R)-3-({[(1Z)-2-tert-butyl-2-{2-[($^2$H$_3$)methyloxy]ethyl}-1-oxido-1λ$^5$-diazan-1-ylidene]amino}oxy)cyclopentanecarboxylic acid (Ex. 6)

(1R,3R)-3-({[(1Z)-2-tert-butyl-2-propyl-1-oxido-1λ$^5$-diazan-1-ylidene]amino}oxy)cyclopentanecarboxylic acid (Ex. 7)

(1R,3R)-3-({[(1Z)-2-tert-butyl-2-butyl-1-oxido-1λ$^5$-diazan-1-ylidene]amino}oxy)cyclopentanecarboxylic acid (Ex. 8)

(1R,3R)-3-({[(1Z)-2-tert-butyl-2-(3-methylbutyl)-1-oxido-1λ$^5$-diazan-1-ylidene]amino}oxy)cyclopentanecarboxylic acid (Ex. 9)

(1S,3R)-3-({[(1Z)-2-tert-butyl-2-methyl-1-oxido-1λ$^5$-diazan-1-ylidene]amino}oxy)cyclopentanecarboxylic acid (Ex. 10)

(1S,3R)-3-({[(1Z)-2-tert-butyl-2-propyl-1-oxido-1λ$^5$-diazan-1-ylidene]amino}oxy)cyclopentanecarboxylic acid Ex. 11)

(1S,3R)-3-({[(1Z)-2-tert-butyl-2-butyl-1-oxido-1λ$^5$-diazan-1-ylidene]amino}oxy)cyclopentanecarboxylic acid (Ex. 12)

(1S,3R)-3-({[(1Z)-2-tert-butyl-2-(2-methoxyethyl)-1-oxido-1λ$^5$-diazan-1-ylidene]amino}oxy)cyclopentanecarboxylic acid (Ex. 13)

(1S,3R)-3-({[(1Z)-2-{2-[(tert-butoxycarbonyl)oxy]ethyl}-2-tert-butyl-1-oxido-1λ$^5$-diazan-1-ylidene]amino}oxy) cyclopentanecarboxylic acid (Ex. 14)

(1S,3R)-3-({[(1Z)-2-(2-aminoethyl)-2-tert-butyl-1-oxido-1λ$^5$-diazan-1-ylidene]amino}oxy)cyclopentanecarboxylic acid (Ex. 15)

(1S,3R)-3-[({(1Z)-2-tert-butyl-1-oxido-2-[2-(1H-1,2,3-triazol-1-yl)ethyl]-1λ$^5$-diazan-1-ylidene}amino)oxy]cyclopentanecarboxylic acid (Ex. 16)

(1R,3S)-3-({[(1Z)-2-tert-butyl-2-ethyl-1-oxido-1λ$^5$-diazan-1-ylidene]amino}oxy)cyclopentanecarboxylic acid (Ex. 17)

(1S,3R)-3-({[(1Z)-2-tert-butyl-2-ethyl-1-oxido-1λ$^5$-diazan-1-ylidene]amino}oxy)cyclopentanecarboxylic acid (Ex. 18)

(1RS,3S,4RS)-3-({[(1Z)-2-tert-butyl-2-methyl-1-oxido-1λ$^5$-diazan-1-ylidene]amino}oxy)-4-fluorocyclopentanecarboxylic acid (Ex. 19)

(1RS,3RS,4RS)-3-({[(1Z)-2-tert-butyl-2-methyl-1-oxido-1λ$^5$-diazan-1-ylidene]amino}oxy)-4-methoxycyclopentanecarboxylic acid (Ex. 20)

(1RS,3RS)-3-({[(1Z)-2-tert-butyl-2-methyl-1-oxido-1λ$^5$-diazan-1-ylidene]amino}oxy)-1-methylcyclopentanecarboxylic acid (Ex. 21)

(1RS,3SR)-3-({[(1Z)-2-tert-butyl-2-ethyl-1-oxido-1λ$^5$-diazan-1-ylidene]amino}oxy)-1-methylcyclopentanecarboxylic acid (Ex. 22)

or pharmaceutically acceptable salts, thereof.

Compounds of the invention can be used to treat hypertension, treat angina, improve insulin sensitivity, and provide renal protection. The compounds can be used alone or in a fixed dose combination with other antihypertensives such as, for example, angiotensin II receptor blockers, diuretics, ACE inhibitors, β-blockers, and calcium channel blockers.

Pharmaceutically acceptable salts include non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, carbonate, cyclopentanepropionate, digluconate, dodecylsulfate, ethanesulfonate, fumarate, glucoheptanoate, gluconate, glycerophosphate, hemisulfate, heptanoate, hexanoate, hippurate, hydrochloride, hydrobromide, hydroiodide, 2-hydroxyethanesulfonate, lactate, lactobionate, laurylsulfate, malate, maleate, mesylate, methanesulfonate, 2-naphthalenesulfonate, nicotinate, nitrate, oleate, oxalate, pamoate, pectinate, persulfate, 3-phenylpropionate, picrate, pivalate, propionate, stearate, succinate, sulfate, tartrate, thiocyanate, tosylate, and undecanoate. Additional specific anionic salts include ascorbate, gluceptate, glutamate, glucoronate, besylate, caprylate, isetionate, gentisate, malonate, napasylate, edfisylate, pamoate, xinafoate, and napadisylate.

Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Additional specific cationic salts include tromethamine, benzathine, benethamine, diethylammonium, epolamine, hydrabamine.

When the compounds of the invention contain one chiral center, the term "stereoisomer" includes both enantiomers and mixtures of enantiomers, such as the specific 50:50 mixture referred to as the racemic mixture. The compounds of the present invention may have multiple chiral centers, providing for multiple stereoisomers. This invention includes all of the stereoisomers and mixtures thereof. Unless specifically mentioned otherwise, reference to one stereoisomer applies to any of the possible stereoisomers. Whenever the stereoisomeric composition is unspecified, all possible stereoisomers are included. Where used, the structure marking "*" indicates the location of a carbon atom that is a chiral center. When bonds to a chiral carbon are depicted as straight lines, it is understood that both (R) and (S) configurations of the chiral carbon, and hence both enantiomers and mixtures thereof, are represented.

Some of the compounds described herein may exist as tautomers. The individual tautomers as well as mixtures thereof are encompassed with the described compounds.

As used herein except where noted, "alkyl" is intended to include both branched- and straight-chain saturated aliphatic hydrocarbon groups having the specified number of carbon atoms. Commonly used abbreviations for alkyl groups are used throughout the specification, e.g. methyl may be represented by conventional abbreviations including "Me" or $CH_3$ or a symbol that is an extended bond as the terminal group, e.g. "⌇—", ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. $C_{1-4}$ alkyl includes n-, iso-, sec- and t-butyl, n- and isopropyl, ethyl and methyl. If no number is specified, 1-4 carbon atoms are intended for linear or branched alkyl groups.

Alkyl groups may be unsubstituted, or substituted with 1 to 3 substituents on any one or more carbon atoms, with halogen, $C_1$-$C_{20}$ alkyl, $CF_3$, $NH_2$, —$NH(C_1$-$C_6$ alkyl), —$N(C_1$-$C_6$ alkyl)$_2$, $NO_2$, oxo, CN, N3, —OH, —$O(C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)S(O)$_{0-2}$—, HS(O)$_{0-2}$—, ($C_1$-$C_6$ alkyl)S(O)$_{0-2}$($C_1$-$C_6$ alkyl)-, HS(O)$_{0-2}$($C_1$-$C_6$ alkyl)-, ($C_1$-$C_6$ alkyl)C(O)NH—, $H_2$N—C(NH)—, —$O(C_1$-$C_6$ alkyl)$CF_3$, HC(O)—, ($C_1$-$C_6$ alkyl)C(O)—, HOC(O)—, ($C_1$-$C_6$ alkyl)OC(O)—, HO($C_1$-$C_6$ alkyl)-, ($C_1$-$C_6$ alkyl)O($C_1$-$C_6$ alkyl)-, ($C_1$-$C_6$ alkyl)C(O)$_{1-2}$($C_1$-$C_6$ alkyl)-, HC(O)$_{1-2}$($C_1$-$C_6$ alkyl)-, ($C_1$-$C_6$ alkyl)C(O)$_{1-2}$—, HOC(O)NH—, ($C_1$-$C_6$ alkyl)OC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound.

The term "aryl", alone or in combination, relates to a phenyl, naphthyl or indanyl group, preferably a phenyl group. The abbreviation "Ph" represents phenyl.

The term "heteroaryl" refers to an unsaturated ring having a specified number of atom members (e.g., 5 or 6-membered), including a specified number of heteroatoms (e.g., 1, 2, 3 or 4 heteroatoms independently selected from N, O or S), e.g., 5-membered rings containing one nitrogen (pyrrole), one oxygen (pyran) or one sulfur (thiophene) atom, 5-membered rings containing one nitrogen and one sulfur (thiazole) atom, 5-membered rings containing one nitrogen and one oxygen (oxazole or isoxazole) atom, 5-membered rings containing two nitrogen (imidazole or pyrazole) atoms, five-membered aromatic rings containing three nitrogen atoms, five-membered aromatic rings containing one oxygen, one nitrogen or one sulfur atom, five-membered aromatic rings containing two heteroatoms independently selected from oxygen, nitrogen and sulfur, 6-membered rings containing one nitrogen (pyridine), or one oxygen (furan) atom, 6-membered rings containing two nitrogen (pyrazine, pyrimidine, or pyridazine) atoms, 6-membered rings containing three nitrogen (triazine) atoms, a tetrazolyl ring; a thiazinyl ring; or coumarinyl. Examples of such ring systems are furanyl, thienyl, pyrrolyl, pyridinyl, pyrimidinyl, indolyl, imidazolyl, triazinyl, thiazolyl, isothiazolyl, pyridazinyl, pyrazolyl, oxazolyl, and isoxazolyl.

The term "heterocyclic" refers to a saturated ring having a specified number of atom members and a specified number of heteroatoms, in which the entire ring system (whether mono- or poly-cyclic) is saturated, e.g., a 4- to 8-membered saturated monocyclic ring or a stable 7- to 12-membered bicyclic ring system which consists of carbon atoms and one or more heteroatoms selected from N, O and S, a 5- or 6-membered heterocyclic ring having 1 or 2 heteroatoms which are N, O or S, etc. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Aryl rings may be unsubstituted, or substituted with 1 substituent on any one or more carbon atoms, with halogen, $C_1$-$C_{20}$ alkyl, $CF_3$, $NH_2$, —$NH(C_1$-$C_6$ alkyl), —$N(C_1$-$C_6$ alkyl)$_2$, $NO_2$, oxo, CN, N3, —OH, —$O(C_1$-$C_6$ alkyl), $C_3$-$C_{10}$ cycloalkyl, $C_2$-$C_6$ alkenyl, $C_2$-$C_6$ alkynyl, HS(O)$_{0-2}$—, ($C_1$-$C_6$ alkyl)S(O)$_{0-2}$—, ($C_1$-$C_6$ alkyl)S(O)$_{0-2}$($C_1$-$C_6$ alkyl)-, HS(O)$_{0-2}$($C_1$-$C_6$ alkyl)-, ($C_1$-$C_6$ alkyl)S(O)$_{0-2}$, ($C_1$-$C_6$ alkyl) C(O)NH—, HC(O)NH—, $H_2$N—C(NH)—, —$O(C_1$-$C_6$ alkyl)$CF_3$, ($C_1$-$C_6$ alkyl)C(O)—, HC(O)—, ($C_1$-$C_6$ alkyl)OC(O)—, HOC(O)—, ($C_1$-$C_6$ alkyl)O($C_1$-$C_6$ alkyl)-, HO($C_1$-$C_6$ alkyl)-, ($C_1$-$C_6$ alkyl)O—, ($C_1$-$C_6$ Heteroaryl and heterocyclic rings may be unsubstituted, or substituted with 1 substituent on any one or more carbon atoms, with halogen, $C_1$-$C_{20}$ alkyl, $CF_3$, $NH_2$, —$NH(C_1$-$C_6$ alkyl), —$N(C_1$-$C_6$ alkyl)$_2$, $NO_2$, oxo, CN, N3, —OH, —$O(C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)S(O)$_{0-2}$—, HS(O)$_{0-2}$—, ($C_1$-$C_6$ alkyl)

alkyl)C(O)$_{1-2}$(C$_1$-C$_6$ alkyl)-, HC(O)$_{1-2}$(C$_1$-C$_6$ alkyl)-, (C$_1$-C$_6$ alkyl)C(O)$_{1-2}$, (C$_1$-C$_6$ alkyl)OC(O)NH—, HOC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl, or independently or additionally substituted with 1 substituent on any one or more nitrogen atoms, with C$_1$-C$_{20}$ alkyl, oxo, C$_3$-C$_{10}$ cycloalkyl, C$_2$-C$_6$ alkenyl, C$_2$-C$_6$ alkynyl, aryl, —C(O)C$_{1-6}$ alkyl, —C(O)NHC$_1$-C$_6$ alkyl, —C(O)NH$_2$, —C$_1$-C$_6$ alkylC(O)NH$_2$, —C$_1$-C$_6$ alkylOC(O)NH$_2$, or independently or additionally substituted with 1 substituent on any one or more sulfur atoms, with C$_1$-C$_{20}$ alkyl, oxo, C$_3$-C$_{10}$ cycloalkyl, C$_2$-C$_6$ alkenyl, C$_2$-C$_6$ alkynyl, aryl, where such substitution results in formation of a stable compound.

The compounds of the invention are useful for treating hypertension, Pulmonary Arterial Hypertension, congestive heart failure, angina, conditions resulting from excessive water retention, cardiovascular diseases, diabetes, oxidative stress, endothelial dysfunction, cirrhosis, pre-eclampsia, osteoporosis, or nephropathy, comprising administering a compounds of the invention to a patient having such a condition, or being at risk to having such condition The invention also relates to the use of compounds of the invention for the preparation of a medicament for the treatment and/or prophylaxis of the above-mentioned diseases.

The above-mentioned compounds of the invention are also of use in combination with other pharmacologically active compounds comprising angiotensin II receptor antagonists (e.g., losartan, valsartan, candesartan, irbesartan, olmesartan) angiotensin converting enzyme inhibitors (e.g. alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), neutral endopeptidase inhibitors (e.g., thiorphan and phosphoramidon), aldosterone antagonists, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES1005, ES 8891, SQ 34017, aliskiren ((2S,4S,5S,7S)—N-(2-carbamoyl-2-methylpropyl)-5-amino-4-hydroxy-2,7-diisopropyl-8-[4-methoxy-3-(3-methoxypropoxy)phenyl]-octanamid hemifumarate) SPP600, SPP630 and SPP635), endothelin receptors antagonists, vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, peripheral vasodilators (e.g. hydralazine), lipid lowering agents (e.g., simvastatin, lovastatin, ezetamibe, atorvastatin, pravastatin), metabolic altering agents including insulin sensitizing agents and related compounds (e.g., muraglitazar, glipizide, metformin, rosiglitazone) or with other drugs beneficial for the prevention or the treatment of the above-mentioned diseases including nitroprusside and diazoxide. Such combination can be achieved by combining two active ingredients in a single dosage formulation containing two independent active ingredients, e.g., an angiotensin II receptor antagonist and a nitrooxy cyclopentane derivative of the invention.

The dosage regimen utilizing the compound of the invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the compounds of the invention, when used for the indicated effects, will range between about 0.0125 mg per kg of body weight per day (mg/kg/day) to about 7.5 mg/kg/day, preferably 0.0125 mg/kg/day to 3.75 mg/kg/day, and more preferably 0.3125 mg/kg/day to 1.875 mg/kg/day. For example, an 80 kg patient would receive between about 1 mg/day and 600 mg/day, preferably 1 mg/day to 300 mg/day, more preferably 25 mg/day to 150 mg/day, and more preferably 5 mg/day to 100 mg/day. A suitably prepared medicament for once a day administration would thus contain between 1 mg and 600 mg, preferably between 1 mg and 300 mg, and more preferably between 25 mg and 300 mg, e.g., 25 mg, 50 mg, 100 mg, 150, 200, 250 and 300 mg. Advantageously, the compound of the invention may be administered in divided doses of two, three, or four times daily. For administration twice a day, a suitably prepared medicament would contain between 0.5 mg and 300 mg, preferably between 0.5 mg and 150 mg, more preferably between 12.5 mg and 150 mg, e.g., 12.5 mg, 25 mg, 50 mg, 75 mg, 100 mg, 125 mg and 150 mg.

The compounds of the invention can be administered in such oral forms as tablets, capsules and granules. The compounds of the invention are typically administered as active ingredients in admixture with suitable pharmaceutical binders as described below. % w/w expresses the weight percent of the indicated composition constituent compared to the total composition. Suitable fillers used in these dosage forms include microcrystalline cellulose, silicified microcrystalline cellulose, dicalcium phosphate, lactose, mannitol, and starch, preferably microcrystalline cellulose, dicalcium phosphate, lactose or mixtures thereof. Suitable binders include hydroxypropyl cellulose, hydroxypropyl methyl cellulose, starch, gelatin, natural sugars such as glucose or beta-lactose, corn-sweeteners, natural and synthetic gums such as acacia, tragacanth or sodium alginate, carboxymethylcellulose, and polyvinyl pyrrolidone. Lubricants used in these dosage forms include sodium oleate, sodium stearate, magnesium stearate, sodium benzoate, sodium acetate, sodium chloride, sodium stearyl fumarate, stearic acid and the like, preferably magnesium stearate. Suitable coating compositions include aqueous dispersion or organic solution of insoluble polymers such as ethyl cellulose, cellulose acetate, cellulose acetate butyrate and acrylate copolymers commercially known as Eudragit®. Plasticizers include triethyl citrate, dibutyl sebacate, dibutyl phthalate, triacetin and castor oil. Antitacking agents include talc, kaolin, colloidal silica or mixtures thereof.

Methods of Synthesis

Several methods for preparing the compounds of this invention are described in the following Schemes and Examples. Starting materials and intermediates are made from known procedures or as otherwise illustrated.

Scheme 1 describes a convenient method to prepare the sodium diazeniumdiolates of the general structure 1-2 in this invention. The secondary amine 1-1 is treated with nitric oxide at an appropriate temperature such as room temperature in the presence of a suitable base such as sodium hydroxide, sodium methoxide, or sodium tert-butoxide in an appropriate solvent such as acetonitrile, methanol, tetrahydrofuran, N,N-dimethylformamide, or water. Examples on the preparation of the sodium diazeniumdiolates can be found from the literature (Chakrapani, H.; Showalter, B. M.; Citro, M. L.; Keefer, L. K.; Saavedra, J. E. *Org. Lett.* 2007, 9, 4551-4554 and WO Patent 2009/094242.

Scheme 1

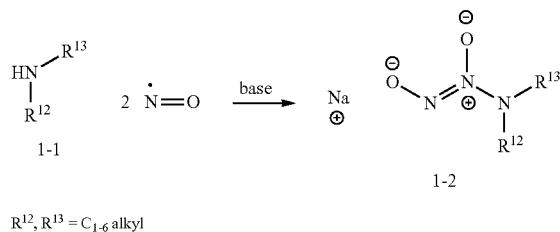

$R^{12}, R^{13} = C_{1-6}$ alkyl

Scheme 2 delineates a method to prepare $O^2$-alkylated diazeniumdiolates of the general structure 2-3 in this invention. Cyclopentanols of the general structure 2-1 can be prepared from reduction of the corresponding ketone, hydroboration/oxidation of the corresponding olefin, and ring opening of the corresponding epoxide. The alcohol 2-1 can be activated for displacement at an appropriate temperature such as room temperature with a suitable reagent such as methanesulfonic anhydride, benzenesulfonyl chloride, 4-(trifluoromethyl)phenylsulfonyl chloride in the presence or absence of a base such as N,N-diisopropylethylamine, triethylamine, N-methylmorpholine, pyridine, or lutidine in an appropriate solvent such as dichloromethane, dichloroethane, chloroform, acetonitrile, tetrahydrofuran, dioxane, toluene, N,N-dimethylformamide, or N-methylpyrrolidinone. The resultant sulfonate 2-2 can be displaced by the appropriate sodium diazeniumdiolate salt 1-2 at an appropriate temperature such as room temperature in an appropriate solvent such as dichloromethane, dichloroethane, chloroform, acetonitrile, tetrahydrofuran, dioxane, toluene, N,N-dimethylformamide, or N-methylpyrrolidinone. The stereochemistry at the sulfonate carbon is typically inverted as a result of the displacement.

Scheme 2

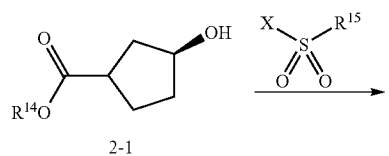

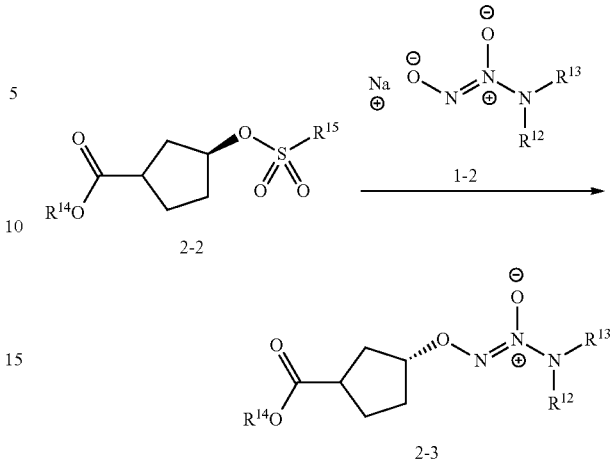

$X = Cl, OSO_2R^{15}$
$R^{14} = C_{1-6}$ alkyl, benzyl
$R^{15} = $ methyl, $CF_3$, substituted phenyl
$R^{12}$ and $R^{13}$ are as defined in Scheme 1.

Scheme 3 describes a method to prepare $O^2$-alkylated diazeniumdiolates of the general structure 3-5 in this invention. Organoboranes such as arylboronic acids, lithium trimethylarylborates, or potassium aryltrifluoroborate can be added to cyclopentenone under the catalysis of a rhodium complex, such as bis(norbornadiene)rhodium tetrafluoroborate, acetylacetonatobis(ethylene)rhodium(I), or chloro-(1,5-cyclooctadiene)rhodium(I)dimer, with an appropriate chiral ligand, such as 2,2'-bis(diphenylphosphino)-1,1'-binaphthyl, 2,2'-bis(diphenylphosphino)-6,6'-dimethoxy-1,1'-biphenyl, or 2,5-dibenzylbicyclo[2.2.1]hepta-2,5-diene in an appropriate solvent such as tetrahydrofuran, dioxane, or toluene with high enantioselectivity. A review of some representative asymmetric catalytic systems capable of achieving high enantioselectivity for the transformation can be found in Hayashi, T.; Yamasaki, K. *Chem. Rev.* 2003, 103, 2829-2844 and Shintani, R.; Hayashi, T. *Aldrichimica Acta* 2009, 2, 31-38. The ketone 3-1 can be reduced to the alcohol 3-2 either with conventional hydride donors such as sodium borohydride or lithium aluminium hydride followed by enzymatic resolution, or in one-step with an enzymatic reducing system or stoichiometric or catalytic amount of organometallic reducing agents that can effect the reduction with high enantioselectivity. The alcohol 3-2 can be activated for displacement at an appropriate temperature such as room temperature with a suitable reagent such as methanesulfonic anhydride, benzenesulfonyl chloride, 4-(trifluoromethyl)phenylsulfonyl chloride in the presence or absence of a base such as N,N-diisopropylethylamine, triethylamine, N-methylmorpholine, pyridine, or lutidine in an appropriate solvent such as dichloromethane, dichloroethane, chloroform, acetonitrile, tetrahydrofuran, dioxane, toluene, N,N-dimethylformamide, or N-methylpyrrolidinone. The resultant sulfonate 3-3 can be displaced by the appropriate sodium diazeniumdiolate salt 1-2 at an appropriate temperature such as room temperature in an appropriate solvent such as dichloromethane, dichloroethane, chloroform, acetonitrile, tetrahydrofuran, dioxane, toluene, N,N-dimethylformamide, or N-methylpyrrolidinone. The stereochemistry at the sulfonate carbon is typically inverted as a result of the displacement. Finally, the aryl group is oxidized to the carboxylic acid with a catalytic amount of ruthenium salt, such as ruthenium(III) chloride or ruthenium (IV) oxide, and a stoichiometric oxidant such as sodium periodate.

Scheme 3

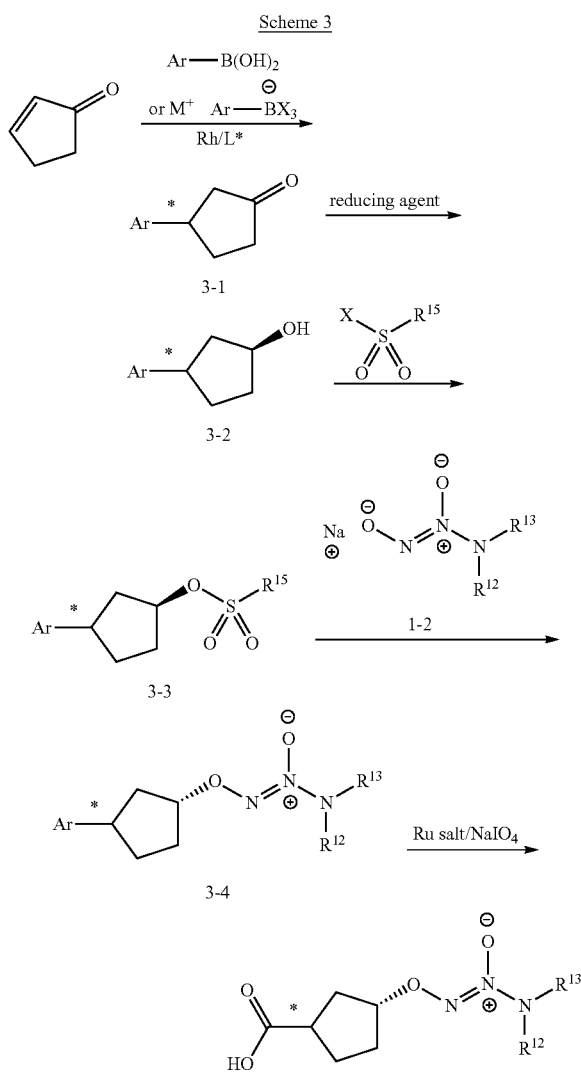

X = Cl, OSO₂R¹⁵
R¹⁵ = methyl, CF₃, substituted phenyl
Ar = aryl
R¹² and R¹³ are as defined in Scheme 1.

Scheme 4 describes a method to prepare functionalized O²-alkylated diazeniumdiolates of the general structure 4-4 in this invention. cis-Diols 4-2 can be prepared from cis-dihydroxylation of olefins 4-1 by stoichiometric osmium tetroxide or catalytic osmium tetroxide with an appropriate stoichiometric oxidant such as 4-methylmorpholine N-oxide, sodium ferricyanate, or tert-butyl hydroperoxide. Cyclic sulfates 4-3 can be prepared from these diols 4-2 with thionyl chloride followed by oxidation of the resultant cyclic sulfite with a catalytic ruthenium salt such as ruthenium(III) chloride or ruthenium(IV) oxide with a stoichiometric oxidant such as sodium periodate. These cyclic sulfates 4-3 can be opened by the appropriate sodium diazeniumdiolate salt 1-2 at an appropriate temperature such as room temperature in an appropriate solvent such as dichloromethane, dichloroethane, chloroform, acetonitrile, tetrahydrofuran, dioxane, toluene, N,N-dimethylformamide, or N-methylpyrrolidinone to afford 4-4. The hydroxyl group present serves as a handle for further functionalization.

Scheme 4

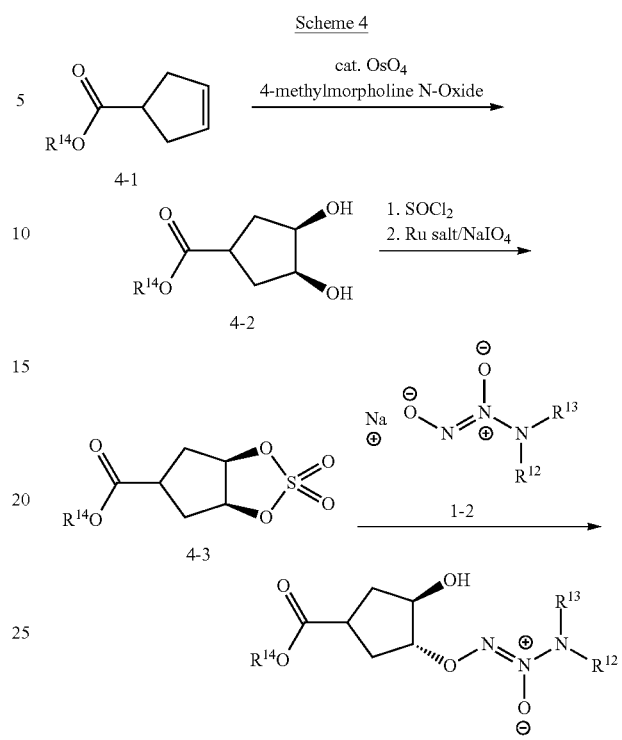

R¹² and R¹³ are as defined in Scheme 1.
R¹⁴ is as defined in Scheme 2.

Abbreviations used in the examples below include DMAP (4-(N,N-dimethylamino)pyridine), DMF (N,N-dimethylformamide), NAD (nicotinamide adenine dinucleotide), DMSO (dimethyl sulfoxide), BINAP (2,2'-bis(diphenylphosphino)-1,1'-binaphthyl) TFA (trifluoroacetic acid), Ac (acetyl), SFC (Supercritical Fluid Chromatography), rt (room temperature), hr (hour), LC (liquid chromatography), THF (tetrahydrofuran), and TBAF (tetra-n-butylammonium fluoride).

Example 1

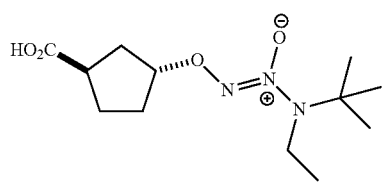 [SMILES: CCN(/[N+]([O-])=N/O[C@@H]1CC[C@@H](C(=O)O)C1)C(C)(C)C]

(1R,3R)-3-({[(1Z)-2-tert-butyl-2-ethyl-1-oxido-1λ⁵-diazan-1-ylidene]amino}oxy)cyclopentanecarboxylic acid Step A: ethyl cis-3-hydroxycyclopentanecarboxylate To a solution of ethyl 3-oxocyclopentanecarboxylate (10.0 g, 64.0 mmol) in 200 ml ethanol at 0° C. was added NaBH₄ (2.91 g, 77.0 mmol) in several portions. The mixture was stirred at 0° C. for 2 hr and then it was concentrated. The residue was partitioned between ether (300 ml) and water (300 ml). The organic layer was separated, washed with brine, dried over MgSO$_4$, and concentrated. The residue was purified by flash chromatography using 0 to 20% EtOAc/hexane gradient, affording the title compound.

Step B: ethyl cis-3-({[4(trifluoromethyl)phenyl]sulfonyl}oxy)cyclopentanecarboxylate To a solution of ethyl cis-3-hydroxycyclopentanecarboxylate (9.7 g, 61.3 mmol) in 500 ml CH$_2$Cl$_2$ at 0° C. was added Et$_3$N (9.31 g, 92.0 mmol) and DMAP (0.75 g, 6.13 mmol), followed by 4-(trifluoromethyl)benzenesulfonyl chloride (16.5 g, 67.4 mmol). After stirring at 0° C. for 1 hr and then at rt for 1 hr, the mixture was concentrated and the residue was partitioned between ether (300 ml) and water (300 ml). The organic layer was washed with brine, dried over MgSO$_4$, and concentrated. The residue was purified by flash chromatography on silica gel using 0 to 30% EtOAc/hexane gradient, affording the title compound: $^1$H NMR (500 MHz, CDCl$_3$) δ 8.07 (d, J=8.2 Hz, 2H), 7.85 (d, J=8.2 Hz, 2H), 5.07 (m, 1H), 4.14 (m, 2H), 3.02 (m, 1H), 2.20-1.85 (m, 6H), 1.26 (m, 3H).

Step C: ethyl (1R,3R)-3-({[(1Z)-2-tert-butyl-2-ethyl-1-oxido-1λ$^5$-diazan-1-ylidene]amino}oxy)cyclopentanecarboxylate To a solution of ethyl cis-3-({[4(trifluoromethyl)phenyl]sulfonyl}oxy)cyclopentanecarboxylate (8.2 g, 22.4 mmol) in 100 ml DMF was added sodium 1-(N-tert-butylethylamino)diazen-1-ium-1,2-diolate (4.92 g, 26.9 mmol). After stirring at 45° C. for 16 hr, the mixture was partitioned between ether (300 ml) and water (300 ml). The organic layer was washed with brine, dried over MgSO$_4$, and concentrated. The residue was purified by flash chromatography on silica gel using 0 to 30% EtOAc/hexane gradient, affording the title compound. $^1$H NMR (500 MHz, CDCl$_3$) δ 4.02 (m, 1H), 2.99 (m, 2H), 2.91 (m, 1H), 2.12-1.73 (m, 6H), 1.12 (m, 9H), 0.92 (m, 3H). The enantiomeric mixture was separated by SFC with chiral IA column, eluting with 10% 2:1:1 heptane:MeOH:EtOH/CO$_2$, to give ethyl (1S,3S)-3-({[(1Z)-2-tert-butyl-2-ethyl-1-oxido-1λ$^5$-diazan-1-ylidene]amino}oxy)cyclopentanecarboxylate as the fast elute compound and ethyl (1R,3R)-3-({[(1Z)-2-tert-butyl-2-ethyl-1-oxido-1λ$^5$-diazan-1-ylidene]amino}oxy)cyclopentanecarboxylate as the slow elute compound. The absolute stereochemistry of these enantiomers was assigned based on the products prepared according to the asymmetric synthetic procedure described in EXAMPLE 5.

Step D: (1R,3R)-3-({[(1Z)-2-tert-butyl-2-ethyl-1-oxido-1λ$^5$-diazan-1-ylidene]amino}oxy)cyclopentanecarboxylic acid To a solution of (1R,3R)-3-({[(1Z)-2-tert-butyl-2-ethyl-1-oxido-1λ$^5$-diazan-1-ylidene]amino}oxy)cyclopentanecarboxylate (1.1 g, 3.65 mmol) (the slow eluting compound of Step C) in 10 ml ethanol at rt was added 5N NaOH (2.0 ml, 10.0 mmol). After stirring at rt for 3 hr, the mixture was concentrated. The residue was partitioned between ether (30 ml) and 1N HCl (20 ml). The organic layer was washed with brine, dried over MgSO$_4$, and concentrated to give the title compound: $^1$H NMR (500 MHz, CDCl$_3$) δ 5.00 (m, 1H), 3.11 (m, 3H), 2.30-1.90 (m, 6H), 1.25 (m, 9H), 1.05 (m, 3H).

Example 2

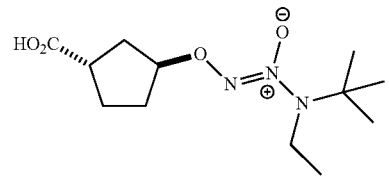 [SMILES: CCN(/[N+]([O-])=N/O[C@H]1CC[C@H](C(=O)O)C1)C(C)(C)C]

(1S,3S)-3-({[(1Z)-2-tert-butyl-2-ethyl-1-oxido-1λ$^5$-diazan-1-ylidene]amino}oxy)cyclopentanecarboxylic acid To a solution of ethyl (1S,3S)-3-({[(Z)-2-tert-butyl-2-ethyl-1-oxido-1λ$^5$-diazan-1-ylidene]amino}oxy)cyclopentanecarboxylate (0.78 g, 2.59 mmol) (the fast eluting compound, EXAMPLE 1 Step C) in 10 ml ethanol at rt was added 5N NaOH (2.0 ml, 10.0 mmol). After stirring at rt for 3 hr, the mixture was concentrated. The residue was partitioned between ether (30 ml) and 1N HCl (20 ml). The organic layer was washed with brine, dried over MgSO$_4$, and concentrated to give the title compound: $^1$H NMR (500 MHz, CDCl$_3$) δ 5.00 (m, 1H), 3.11 (m, 3H), 2.30-1.90 (m, 6H), 1.25 (m, 9H), 1.05 (m, 3H).

Example 3 and 4

(1R,3R)-3-({[(1Z-2-tert-butyl-2-methyl-1-oxido-1λ$^5$-diazan-1-ylidene]amino}oxy)cyclopentanecarboxylic acid (Example 3) and (1S,3S)-3-({[(1Z)-2-tert-butyl-2-methyl-1-oxido-1λ$^5$-diazan-1-ylidene]amino}oxy)cyclopentanecarboxylic acid (Example 4)

The following examples were prepared using procedures analogous to those described for EXAMPLE 1 and 2 substituting sodium 1-(N-tert-butylmethylamino)diazen-1-ium-1,2-diolate for sodium 1-(N-tert-butylethylamino)diazen-1-ium-1,2-diolate in Step C.

| EXAMPLE # | $t_R$ (min) | LCMS |
| --- | --- | --- |
| 3 | 2.48 | 323.14[M + 23] |
| 4 | 2.48 | 323.14[M + 23] |

Example 5

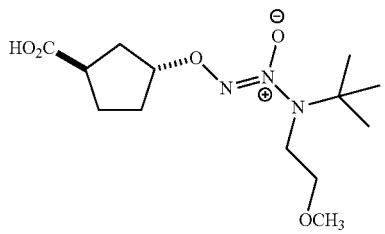 [SMILES: COCCN(/[N+]([O-])=N/O[C@@H]1CC[C@@H](C(=O)O)C1)C(C)(C)C]

(1R,3R)-3-({[(1Z)-2-tert-butyl-2-(2-methoxyethyl)-1-oxido-1λ⁵-diazan-1-ylidene]amino}oxy)cyclopentanecarboxylic acid

Step A: (3R)-3-(4-methoxyphenyl)cyclopentanone

To a solution of cyclopent-2-en-1-one (1.0 mL, 12.4 mmol), 4-methoxyphenylboronic acid (3.76 g, 24.7 mmol), and (R)-BINAP (0.46 g, 0.74 mmol) in a mixture of 1,4-dioxane (20 mL) and water (2 mL) at rt was added ruthenium (0.19 g, 0.74 mmol). After stirring at 100° C. overnight, the mixture was cooled down to rt and partitioned between ether (100 mL) and sat. NaHCO₃ (100 mL). The organic layer was separated, washed with sat. NaHCO₃ and brine, dried over MgSO₄, and concentrated. The residue was purified by flash chromatography on silica gel using 0 to 30% EtOAc/hexane gradient, affording the title compound: ¹H NMR δ 7.20 (d, J=8.6 Hz, 2H), 6.91 (d, J=8.7 Hz, 2H), 3.83 (s, 3H), 3.40 (m, 1H), 2.66 (m, 1H), 2.46 (m, 2H), 2.33 (m, 2H), 1.97 (m, 1H).

Step B: (1S,3R)-3-(4-methoxyphenyl)cyclopentanol

To a 2 L 3-neck round bottom flask with thermocouple, heating mantle, and overhead stirrer was charged 47.41 g of starting (3R)-3-(4-methoxyphenyl)cyclopentanone was added 475 mL of 0.5M, pH=6.5 phosphate buffer. To a solution of sodium formate (33.9 g) in 475 mL of 0.5M, pH=6.5 phosphate buffer in a 1.0 L Erlenmeyer flask was added nicotinamide adenine dinucleotide (NAD) (975 mg), formate hydrogenase 101 (1.95 g, Codexis) and ketoreductase NAD dependent 102 (975 mg, Biocatalytics). After adding the enzyme containing solution to the reaction flask, the reaction mixture was heated to 30° C. After overnight age, LC showed >98% conversion. Heating was discontinued and K₂CO₃ (285 g) was added to the reaction mixture. The mixture was transferred to a separation funnel and was dilute with acetonitrile (950 mL). The organic layer was separated and filtered through powdered cellulose. The residue was washed with acetonitrile (425 mL), which was used to back extract the aqueous layer. The initial organic layer and the back extraction were combined and concentrated to give the title compound: ¹H NMR δ 7.23 (d, J=8.7 Hz, 2H), 6.87 (d, J=8.7 Hz, 2H), 4.46 (m, 1H), 3.82 (s, 3H), 3.03 (m, 1H), 2.49 (m, 1H), 2.07-1.80 (m, 5H), 1.65 (m, 1H).

Step C: (1S,3R)-3-(4-methoxyphenyl)cyclopentyl 4-(trifluoromethyl)benzenesulfonate To a solution of (1S,3R)-3-(4-methoxyphenyl)cyclopentanol (1.19 g, 6.2 mmol), triethylamine (0.86 mL, 6.2 mmol), and DMAP (0.76 g, 6.2 mmol) in CH₂Cl₂ (20 mL) at 0° C. was added 4-(trifluoromethyl)benzenesulfonyl chloride (1.5 g, 6.2 mmol). After stirring at rt overnight, the mixture was partitioned between Et₂O and sat. NaHCO₃. The organic layer was separated, washed with brine, dried over MgSO₄, and concentrated. The residue was purified by flash chromatography on silica gel using 0-30% EtOAc in hexanes to give the title compound: ¹H NMR (500 MHz, CDCl₃) δ 8.08 (d, J=8.3 Hz, 2H), 7.85 (d, J=8.2 Hz, 2H), 7.14 (d, J=8.6 Hz, 2H), 6.85 (d, J=8.6 Hz, 2H), 5.15 (m, 1H), 3.81 (s, 3H), 3.00 (m, 1H), 2.50 (m, 1H), 2.09-1.80 (m, 5H).

Step D: 2-{tert-butyl[(Z)-{[(1R,3R)-3-(4-methoxyphenyl)cyclopentyl]oxy}-NNO-azoxy]amino}ethanol

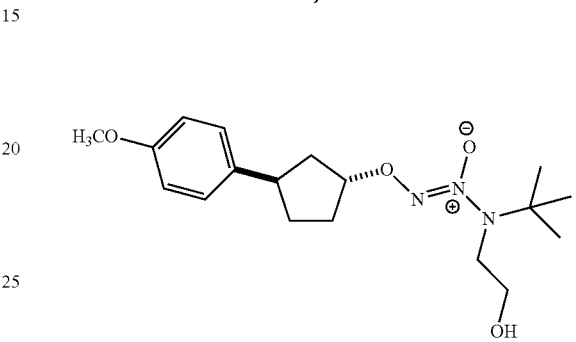

To a solution of (1S,3R)-3-(4-methoxyphenyl)cyclopentyl 4-(trifluoromethyl)benzenesulfonate (10.0 g, 24.97 mmol) in DMSO (100 mL) was added sodium 1-(N-tert-butyl-N-(2-hydroxyethyl)amino)diazen-1-ium-1,2-diolate (7.46 g, 37.5 mmol). After stirring at rt for 16 hr, the mixture was partitioned between Et₂O (300 ml) and water (300 ml), washed with brine, dried over MgSO₄, filtered and concentrated. The residue was purified by flash chromatography on silica gel using 0 to 30% EtOAc/hexane gradient, affording the title compound: ¹H NMR (500 MHz, CDCl₃) δ 7.16 (d, J=8.6 Hz, 2H), 6.86 (d, J=8.6 Hz, 2H), 5.05 (m, 1H), 3.81 (s, 3H), 3.59 (m, 2H), 3.34 (m, 1H), 3.28 (m, 2H), 2.36 (m, 3H), 2.25 (m, 1H), 2.02 (m, 1H), 1.90 (m, 1H), 2.65 (m, 1H), 1.29 (s, 9H).

Step E: N-(2-methoxyethyl)-N—[(Z)-{[(1R,3R)-3-(4-methoxyphenyl)cyclopentyl]oxy}-NNO-azoxy]-2-methylpropan-2-amine

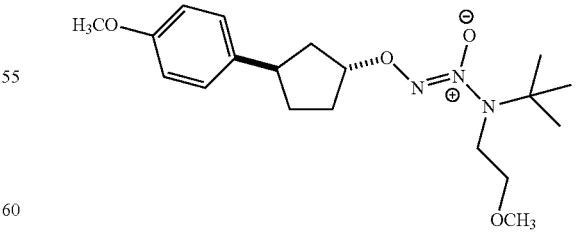

To a solution of 2-{tert-butyl[(Z)-{[(1R,3R)-3-(4-methoxyphenyl)cyclopentyl]oxy}-NNO-azoxy]amino}ethanol (1 g, 2.85 mmol) in 10 ml DMF at 0° C. was added NaH (0.13 g, 3.56 mmol), after 10 min, MeI (0.22 mL, 3.56 mmol) was added. The mixture was gradually warmed up to rt and stirred over night. The reaction mixture was partitioned between Et₂O (30 ml) and water (30 ml), washed with brine, dried over MgSO₄, filtered and concentrated. The residue was purified by flash chromatography on silica gel using 0 to 30% EtOAc/hexane gradient, affording the title compound: ¹H NMR (500 MHz, CDCl₃) δ 7.13 (d, J=8.6 Hz, 2H), 6.84 (d, J=8.6 Hz, 2H), 5.05 (m, 1H), 3.77 (s, 3H), 3.40 (m, 2H), 3.33 (s, 3H), 3.29 (m, 3H), 2.36 (m, 1H), 2.30 (m, 1H), 2.20 (m, 1H), 2.00 (m, 1H), 1.85 (m, 1H), 1.60 (m, 1H), 1.26 (s, 9H).

Step F: (1R,3R)-3-({[(1Z)-2-tert-butyl-2-(2-methoxyethyl)-1-oxido-1λ⁵-diazan-1-ylidene]amino}oxy)cyclopentanecarboxylic acid To a solution of sodium periodate (4.682 g, 21.89 mmol) in 12 ml water was added acetonitrile (8 ml), a solution of N-(2-methoxyethyl)-N—[(Z)-{[(1R,3R)-3-(4-methoxyphenyl)cyclopentyl]oxy}-NNO-azoxy]-2-methylpropan-2-amine (400 mg, 1.094 mmol) in CCl₄ (8 ml), and followed by ruthenium (III) chloride hydrate (24.67 mg, 0.109 mmol). After stirring at rt for 30 min, the reaction mixture was partitioned between Et₂O and 1N HCl. The aqueous layer was separated and extracted with ether. The organic layers were combined, dried over MgSO4, filtered and concentrated. The residue was purified by flash chromatography on silica gel using 0-70% EtOAc in hexane to give the title compound as oil: ¹H NMR (500 MHz, CDCl₃) δ 4.92 (m, 1H), 3.33 (m, 2H), 3.27 (s, 3H), 3.21 (m, 2H), 3.00 (m, 1H), 2.22-1.83 (m, 6H), 1.17 (s, 9H).

Example 6

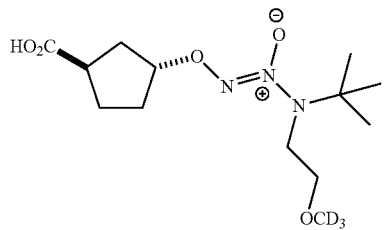

(1R,3R)-3-({[(1Z)-2-tert-butyl-2-{2-[(²H₃)methyloxy]ethyl}-1-oxido-1λ⁵-diazan-1-ylidene]amino}oxy)cyclopentanecarboxylic acid EXAMPLE 6 was prepared using the same procedure analogous to EXAMPLE 5 substituting deuterated methyl iodide for methyl iodide in Step E: ¹H NMR (500 MHz, CDCl₃) δ 4.95 (m, 1H), 3.36 (m, 2H), 3.24 (m, 2H), 3.03 (m, 1H), 2.25-1.83 (m, 6H), 1.20 (s, 9H).

Example 7-9

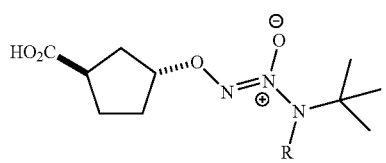

(1R,3R)-3-({[(1Z)-2-tert-butyl-2-propyl-1-oxido-1λ⁵-diazan-1-ylidene]amino}oxy)cyclopentanecarboxylic acid (Example 7) (1R,3R)-3-({[(Z)-2-tert-butyl-2-butyl-1-oxido-1λ⁵-diazan-1-ylidene]amino}oxy)cyclopentanecarboxylic acid (Example 8), and (1R,3R)-3-({[(1Z)-2-tert-butyl-2-(3-methylbutyl)-1-oxido-1λ⁵-diazan-1-ylidene]amino}oxy)cyclopentanecarboxylic acid (Example 9)

The following examples were prepared using procedures analogous to those described for EXAMPLE 5 by substituting the appropriate sodium salt for sodium 1-(N-tert-butyl-N-(2-hydroxyethyl)amino)diazen-1-ium-1,2-diolate, DMF for DMSO, and reaction temperature 40-50° C. for rt in Step D.

| EXAMPLE # | R | $t_R$ (min) | LCMS |
|---|---|---|---|
| 7 | ⌇⌇⌇—CH₂—CH₂—CH₃ | 3.26 | 310.16 [M + 23] |
| 8 | ⌇⌇⌇—CH₂—CH₂—CH₂—CH₃ | 3.16 | 324.03 [M + 23] |
| 9 | ⌇⌇⌇—CH₂—CH₂—CH(CH₃)CH₃ | 3.29 | 338.15 [M + 23] |

Example 10-12

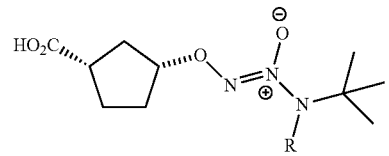

(1S,3R)-3-({[(1Z)-2-tert-butyl-2-methyl-1-oxido-1λ⁵-diazan-1-ylidene]amino}oxy)cyclopentanecarboxylic acid (Example 10)

(1S,3R)-3-({[(1Z)-2-tert-butyl-2-propyl-1-oxido-1λ⁵-diazan-1-ylidene]amino}oxy) cyclopentanecarboxylic acid (Example 11), and (1S,3R)-3-({[(1Z)-2-tert-butyl-2-butyl-1-oxido-1λ⁵-diazan-1-ylidene]amino}oxy)cyclopentanecarboxylic acid (Example 12)

The following examples were prepared using procedures analogous to those described for EXAMPLE 5 substituting (S)-BINAP for (R)-BINAP in Step A and appropriate sodium salt for sodium 1-(N-tert-butyl-N-(2-hydroxyethyl)amino)diazen-1-ium-1,2-diolate, DMF for DMSO, and reaction temperature 40-50° C. for rt in Step D.

| EXAMPLE # | R | $t_R$ (min) | LCMS |
|---|---|---|---|
| 10 | ⌇-CH(CH3)2 type (isopropyl-like) | 1.26 | 281.79 [M + 23] |
| | <sup>1</sup>H NMR (500 MHz, CDCl<sub>3</sub>): δ 4.91-4.86 (m, 1H), 2.93-2.87 (m, 1H), 2.80 (s, 3H), 2.45-2.25 (m, 2H), 2.26-2.10 (m, 2H), 2.07-1.87 (m, 2H), 1.13 (s, 9H). | | |
| 11 | ⌇-CH2CH2CH3 | 1.67 | 309.82 [M + 23] |
| | <sup>1</sup>H NMR (500 MHz, CDCl<sub>3</sub>): δ 4.93-4.88 (m, 1H), 3.01 (t, J = 7.4 Hz, 2H), 2.91-2.83 (m, 1H), 2.42-2.33 (m, 1H), 2.31-2.24 (m, 1H), 2.20-2.06 (m, 2H), 2.05-1.88 (m, 2H), 1.43-1.39 (m, 2H), 1.25 (s, 9H), 0.95 (t, J = 7.4 Hz, 3H). | | |
| 12 | ⌇-CH2CH2CH2CH3 | 1.83 | 323.83 [M + 23] |
| | <sup>1</sup>H NMR (500 MHz, CDCl<sub>3</sub>): δ 4.91-4.88 (m, 1H), 3.03 (t, J = 6.5 Hz, 2H), 2.86 (q, J = 8.3 Hz, 1H), 2.42-2.32 (m, 1H), 2.32-2.05 (m, 3H), 2.04-1.88 (m, 2H), 1.37 (m, 4H), 1.24 (s, 9H), 0.92 (t, J = 6.6 Hz, 3H). | | |

Example 13

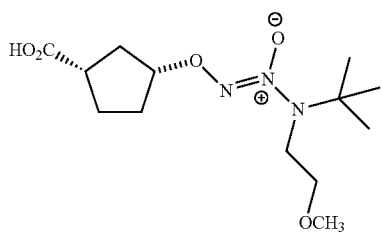 [SMILES: COCCN(/[N+]([O-])=N/O[C@@H]1CC[C@H](C(=O)O)C1)C(C)(C)C]

(1S,3R)-3-({[(1Z)-2-tert-buty-2-(2-methoxyethyl)-1-oxido-1λ<sup>5</sup>-diazan-1-ylidene]amino}oxy)cyclopentanecarboxylic acid The title compound was prepared according to the procedures described in EXAMPLE 5 substituting (S)-BINAP for (R)-BINAP in Step A: <sup>1</sup>H NMR (500 MHz, CDCl<sub>3</sub>): δ 8.24 (bs, 1H), 4.96-4.92 (m, 1H), 3.43 (t, J=5.5 Hz, 2H), 3.37 (s, 3H), 3.30 (t, J=5.4 Hz, 2H), 2.90 (q, J=8.1 Hz, 1H), 2.41-2.27 (m, 2H), 2.24-1.82 (m, 4H), 1.26 (s, 9H).

Example 14

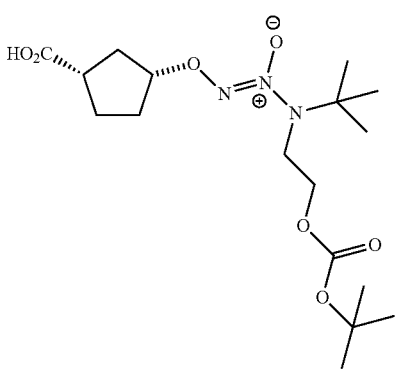 [SMILES: CC(C)(C)OC(=O)OCCN(/[N+]([O-])=N/O[C@@H]1CC[C@H](C(=O)O)C1)C(C)(C)C]

(1S,3R)-3-({[(1Z)-2-{2-[(tert-butoxycarbonyl)oxy]ethyl}-2-tert-butyl-1-oxido-1λ<sup>5</sup>-diazan-1-ylidene]amino}oxy)cyclopentanecarboxylic acid Step A: tert-butyl 2-{tert-butyl[(Z)-{[(1S,3R)-3-(4-methoxyphenyl)cyclopentyl]oxy}-NNO-azoxy]amino}ethyl carbonate A solution of 2-{tert-butyl[(Z)-{[(1S,3R)-3-(4-methoxyphenyl)cyclopentyl]oxy}-NNO-azoxy]amino}ethanol (0.82 g, 2.33 mmol), prepared according to Example 5 step D substituting (S)-BINAP for (R)-BINAP in step A, di-tert-butyl dicarbonate (0.66 g, 3.03 mmol), DMAP (0.057 g, 0.467 mmol), and triethylamine (0.425 g, 4.20 mmol) were stirred under nitrogen in CH<sub>2</sub>Cl<sub>2</sub> (5 mL). The reaction mixture was stirred at rt overnight. The reaction mixture was partitioned between ethyl acetate and 10% aqueous citric acid. The organic layer was washed with water and brine. The organic layer was dried over sodium sulfate, filtered and evaporated. The crude was chromatographed on silica gel, eluting with hexane-ethyl acetate (0-100%, 2 L), to afford the title compound: <sup>1</sup>H NMR (500 MHz, CDCl<sub>3</sub>): δ 7.24-7.13 (m, 2H), 6.87 (d, J=8.3 Hz, 2H), 5.08-4.98 (m, 1H), 4.08 (t, J=5.8 Hz, 2H), 3.82 (s, 3H), 3.48-3.33 (m, 2H), 3.09-2.99 (m, 1H), 2.65-2.55 (m, 1H), 2.19-2.12 (m, 1H), 2.09-1.96 (m, 2H), 1.99-1.81 (m, 2H), 1.48 (s, 9H), 1.27 (s, 9H).

Step B: (1S,3R)-3-({[(1Z)-2-{2-[(tert-butoxycarbonyl)oxy]ethyl}-2-tert-butyl-1-oxido-1λ<sup>5</sup>-diazan-1-ylidene]amino}oxy)cyclopentanecarboxylic acid The title compound was prepared according to the method described in EXAMPLE 5 Step F using tert-butyl 2-{tert-butyl[(Z)-{[(1S,3R)-3-(4-methoxyphenyl)cyclopentyl]oxy}-NNO-azoxy]amino}ethyl carbonate as the starting material: <sup>1</sup>H NMR (500 MHz, CDCl<sub>3</sub>): δ 6.60-6.01 (bs, 1H), 4.93-4.90 (m, 1H), 4.09-4.05 (m, 2H), 3.40 (t, J=5.9 Hz, 2H), 2.89 (q, J=8.1 Hz, 1H), 2.37-2.26 (m, 2H), 2.26-2.07 (m, 3H), 2.08-1.86 (m, 1H), 1.46 (s, 9H), 1.13 (s, 9H).

Example 15

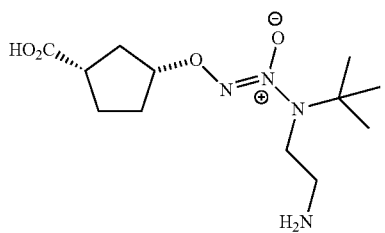 [SMILES: CC(C)(C)N(CCN)/[N+]([O-])=N/O[C@@H]1CC[C@H](C(=O)O)C1]

(1S,3R)-3-({[(1Z)-2-(2-aminoethyl-2-tert-butyl-1-oxido-1λ⁵-diazan-1-ylidene]amino}oxy)cyclopentanecarboxylic acid Step A: N-(2-azidoethyl)-N—[(Z)-{[(1S,3R)-3-(4-methoxyphenyl)cyclopentyl]oxy}-NNO-azoxy]-2-methylpropan-2-amine The title compound was prepared according to the method described in EXAMPLE 5 step D using 2-{tert-butyl[(Z)-{[(1S,3R)-3-(4-methoxyphenyl)cyclopentyl]oxy}-NNO-azoxy]amino}ethanol (3.6 g, 10.24 mmol) substituting (S)-BINAP for (R)-BINAP in step A, and reacting it with Zn(N₃)₂.2Py (4.7 g, 15.3 mmol), triphenylphosphine (5.37 g, 20.49 mmol), in anhydrous toluene diisopropyl azodicarboxylate (4.14 g, 20.49 mmol) in anhydrous toluene. The reaction mixture was stirred until complete consumption of the alcohol. The mixture was filtered over a pad of diatomaceous earth, concentrated in vacuo and purified by column chromatography eluting with hexane/ethyl acetate 0-100%) to give the title compound: ¹H NMR (500 MHz, CDCl₃): δ 7.20 (d, J=8.3 Hz, 2H), 6.85 (d, J=8.3 Hz, 2H), 5.11-5.00 (m, 1H), 3.81 (s, 3H), 3.35-3.25 (m, 41H), 3.11-3.01 (m, 1H), 2.61 (t, J=7.5 Hz, 1H), 2.20-2.19 (m, 1H), 2.19-2.00 (m, 2H), 1.93-1.83 (m, 2H), 1.29 (s, 9H).

Step B: N-tert-butyl-N—[(Z)-{[(1S,3R)-3-(4-methoxyphenyl)cyclopentyl]oxy}-NNO-azoxy]ethane-1,2-diamine To a solution of N-(2-azidoethyl)-N—[(Z)-{[(1S,3R)-3-(4-methoxyphenyl)cyclopentyl]oxy}-NNO-azoxy]-2-methylpropan-2-amine (2.1 g, 5.58 mmol) in methanol was added Raney nickel (Sigma-Aldrich, Raney 2800 nickel, slurry in water, active catalyst). The mixture was stirred at rt and the progress of the reaction was monitored by TLC. Upon completion, the reaction mixture was filtered through diatomaceous earth and the solvent was evaporated. The crude material was used without purification.

Step C: tert-butyl (2-{tert-butyl[(Z)-{[(1S,3R)-3-(4-methoxyphenyl)cyclopentyl]oxy}-NNO-azoxy]amino}ethyl)carbamate To a solution of N-tert-butyl-N—[(Z)-{[(1S,3R)-3-(4-methoxyphenyl)cyclopentyl]oxy}-NNO-azoxy]ethane-1,2-diamine (1.38 g, 3.94 mmol), di-tert-butyl dicarbonate (1.17 g, 5.12 mmol) in methylene chloride was added triethylamine (0.717 g, 7.09 mmol). The mixture was stirred at rt overnight. The reaction mixture was partitioned between ethyl acetate and 10% aqueous citric acid. The organic layer was washed with water and brine. The organic layer was dried over sodium sulfate, filtered and evaporated. The crude was chromatographed on silica gel, eluting with hexane-ethyl acetate (0-100%, 2 L), to afford the title compound: ¹H NMR (500 MHz, CDCl₃): δ 7.29 (s, 1H), 7.19 (d, J=8.2 Hz, 2H), 6.87 (d, J=8.1 Hz, 2H), 4.99 (d, J=9.7 Hz, 1H), 3.81 (s, 3H), 3.23 (m, 2H), 3.14 (m, 2H), 3.11-3.00 (m, 1H), 2.59 (t, J=14.1, 7.5 Hz, 1H), 2.17-1.83 (m, 5H), 1.46 (s, 9H), 1.26 (s, 9H).

Step D: (1S,3R)-3-({[1)-2-(2-aminoethyl)-2-tert-butyl-1-oxido-1λ⁵-diazan-1-ylidene]amino}oxy)cyclopentanecarboxylic acid The title compound was prepared according to the method described in EXAMPLE 5 Step F using tert-butyl (2-{tert-butyl[(Z)-{[(1S,3R)-3-(4-methoxyphenyl)cyclopentyl]oxy}-NNO-azoxy]amino}ethyl)carbamate as the starting material. The isolated compound was treated with TFA (100%) to give the title compound: ¹H NMR (500 MHz, CDCl₃): δ 9.31 (bs, 2H), 7.60 (bs, 1H), 4.96 (m, 1H), 3.49-3.39 (m, 2H), 3.02-2.96 (m, 3H), 2.49-2.45 (m, 1H), 2.01-1.91 (m, 5H), 1.24 (m, 9H).

Example 16

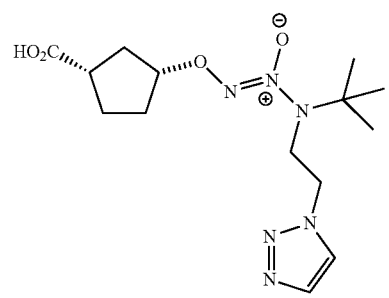 [SMILES: CC(C)(C)N(CCn1ccnn1)/[N+]([O-])=N/O[C@@H]1CC[C@H](C(=O)O)C1]

(1S,3R)-3-[({(1Z)-2-tert-butyl-1-oxido-2-[2-(1H-1,2,3-triazol-1-yl)ethyl]-1λ⁵-diazan-1-ylidene}amino)oxy]cyclopentanecarboxylic acid Step A: N—[(Z)-{[(1S,3R-3-(4-methoxyphenyl)cyclopentyl]oxy}-NNO-azoxy]-2-methyl-N-{2-[4-(trimethylsilyl)-1H-1,2,3-triazol-1-yl]ethyl}propan-2-amine A solution of N-(2-azidoethyl)-N—[(Z)-{[(1S,3R)-3-(4-methoxyphenyl)cyclopentyl]oxy}-NNO-azoxy]-2-methylpropan-2-amine (EXAMPLE 15 Step A, 1.00 g, 2.66 mmol) substituting (S)-BINAP for (R)-BINAP in step A and trimethylsilyl acetylene (0.522 g, 5.31 mmol) in anhydrous toluene was heated at 60° C. overnight. The solvent was evaporated and the crude was chromatographed on silica gel eluting with hexane-ethyl acetate (0-100%, 2 L), to afford the title compound.

Step B: N—[(Z)-{[(1S,3R)-3-(4-methoxyphenyl)cyclopentyl]oxy}-NNO-azoxy]-2-methyl-N-[2-(1H-1,2,3-triazol-1-yl)ethyl]propan-2-amine To a solution of N—[(Z)-{[(1S,3R)-3-(4-methoxyphenyl)cyclopentyl]oxy}-NNO-azoxy]-2-methyl-N-{2-[4-(trimethylsilyl)-1H-1,2,3-triazol-1-yl]ethyl}propan-2-amine (0.960 g, 2.02 mmol) in THF (10 mL) was added TBAF (3.034 mL, 3.034 mmol). The mixture was stirred at rt overnight. The solvent was evaporated and the crude was chromatographed on silica gel eluting with hexane-ethyl acetate (0-100%, 2 L), to afford the title compound.

Step C: (1S,3R)-3-[({(1Z)-2-tert-butyl-1-oxido-2-[2-(H-1,2,3-triazol-1-yl)ethyl]-1λ⁵-diazan-1-ylidene}amino)oxy]cyclopentanecarboxylic acid The title compound was prepared according to the method described in EXAMPLE 5 Step F using N—[(Z)-{[(1S,3R)-3-(4-methoxyphenyl)cyclopentyl]oxy}-NNO-azoxy]-2-methyl-N-[2-(1H-1,2,3-triazol-1-yl)ethyl]propan-2-amine as the starting material: $^1$H NMR (500 MHz, CDCl$_3$): δ 10.96 (bs, 1H), 7.89 (s, 1H), 7.85 (s, 1H), 4.94 (s, 1H), 4.51-4.43 (m, 2H), 3.56-3.49 (m, 2H), 3.01-2.87 (m, 1H), 2.43-2.20 (m, 2H), 2.23-1.91 (m, 4H), 1.13 (s, 9H).

Example 17

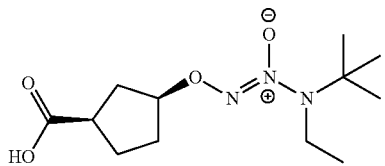 [SMILES: CCN(/[N+]([O-])=N/O[C@H]1CC[C@@H](C(=O)O)C1)C(C)(C)C]

(1R,3S)-3-({[(1Z)-2-tert-butyl-2-ethyl-1-oxido-1λ⁵-diazan-1-ylidene]amino}oxy)cyclopentanecarboxylic acid Step A: benzyl cyclopent-3-ene-1-carboxylate To a N,N-dimethylformamide solution (450 mL) of 3-cyclopentene-1-carboxylic acid (50.0 g, 446 mmol) was added potassium carbonate (126 g, 913 mmol), followed by slow addition of benzyl bromide (80 mL, 669 mmol). After 3 hours, the reaction mixture was poured into 500 mL water and extracted with diethyl ether (3×800 mL). The combined organic extracts were washed with brine, dried (magnesium sulfate), and concentrated in vacuo to afford the title compound in a crude form. It was carried forward to the subsequent reaction without further purification. $^1$H NMR (500 MHz, CDCl$_3$) δ 7.43-7.29 (m, 5H), 5.68 (s, 2H), 5.16 (s, 2H), 3.24-3.14 (m, 1H), 2.73-2.63 (m, 4H).

Step B: benzyl trans-3-hydroxycyclopentanecarboxylate

To a tetrahydrofuran solution (25 mL) of benzyl cyclopent-3-ene-1-carboxylate (11.8 g, 43.3 mmol) in a 250-mL round-bottom flask under nitrogen at 0° C. was added 1.0 M borane tetrahydrofuran complex (22.0 mL, 22.0 mmol) over 15 minutes. The flask was removed from the ice bath and stirred for 2 hours. Water (50 mL) was slowly added to the reaction mixture, followed by the slow addition of sodium perborate tetrahydrate (6.66 g, 43.3 mmol) over 15 minutes. The mixture was stirred overnight 16 hr. Brine (50 mL) was added, and the organic layer was removed. The aqueous white suspension was extracted with ethyl acetate (3×100 mL), and the combined organic extracts were washed with brine, dried (magnesium sulfate), and concentrated in vacuo. Chromatography over silica gel, eluting with hexanes/ethyl acetate, afforded the title compound as a colorless liquid. $^1$H NMR (500 MHz, CDCl$_3$) δ 7.38-7.29 (m, 5H), 5.12 (s, 2H), 4.45 (d, J=4.6 Hz, 1H), 3.16-3.06 (m, 1H), 2.17-1.80 (m, 5H), 1.68-1.61 (m, 1H).

Step C: benzyl trans-3-({[4(trifluoromethyl)phenyl]sulfonyl}oxy)cyclopentanecarboxylate The title compound was made by following the procedures described in EXAMPLE 1, Step B substituting benzyl trans-3-hydroxycyclopentanecarboxylate for ethyl cis-3-hydroxy-cyclopentanecarboxylate. $^1$H NMR (500 MHz, CDCl$_3$) δ 8.03 (d, J=8.2 Hz, 2H), 7.82 (d, J=8.2 Hz, 2H), 7.38-7.29 (m, 5H), 5.15-5.08 (m, 3H), 3.07 (qd, J=8.6, 6.2 Hz, 1H), 2.19-2.06 (m, 3H), 2.02-1.83 (m, 3H).

Step D: benzyl cis-3-({[(1Z)-2-tert-butyl-2-ethyl-1-oxido-1λ⁵-diazan-1-ylidene]amino}oxy)cyclopentanecarboxylate The title compound was made by following the procedures described in EXAMPLE 1, Step C substituting benzyl trans-3-({[4(trifluoromethyl)phenyl]sulfonyl}oxy)cyclopentanecarboxylate for ethyl cis-3-({[4(trifluoromethyl)phenyl]sulfonyl}oxy)cyclopentanecarboxylate. $^1$H NMR (500 MHz, CDCl$_3$) δ 7.40-7.31 (m, 5H), 5.14 (s, 2H), 4.93-4.88 (m, 1H), 3.11 (q, J=7.0 Hz, 2H), 2.87 (quintet, J=8.3 Hz, 1H), 2.41 (ddd, J=14.4, 8.9, 6.6 Hz, 1H), 2.26 (ddd, J=14.3, 8.5, 4.7 Hz, 1H), 2.16-2.05 (m, 2H), 2.01-1.88 (m, 2H), 1.25 (s, 9H), 1.05 (t, J=7.0 Hz, 3H). Separation of the racemic mixture with Chiralpak AD-H column, eluting with 4-40% isopropanol/carbon dioxide, afforded the (1R,3S)-enantiomer as the faster eluting product and the (1S,3R) as the slower eluting product.

Step E: (1R,3S)-3-({[(1Z)-2-tert-butyl-2-ethyl-1-oxido-1λ⁵-diazan-1-ylidene]amino}oxy)cyclopentanecarboxylic acid The title compound was made by following the procedures described in EXAMPLE 1, Step D substituting benzyl (1R,3S)-3-({[(1Z)-2-tert-butyl-2-ethyl-1-oxido-1λ⁵-diazan-1-ylidene]amino}oxy)cyclopentanecarboxylate for ethyl (1S,3S)-3-({[(1Z)-2-tert-butyl-2-ethyl-1-oxido-1λ⁵-diazan-1-ylidene]amino}oxy)cyclopentanecarboxylate. $^1$H NMR (500 MHz, CDCl$_3$) δ 4.93-4.87 (m, 1H), 3.10 (q, J=7.0 Hz, 2H), 2.86 (quintet, J=8.3 Hz, 1H), 2.36 (ddd, J=14.5, 9.1, 6.3 Hz, 1H), 2.27 (ddd, J=14.4, 7.9, 4.3 Hz, 1H), 2.17-2.06 (m, 2H), 2.03-1.87 (m, 2H), 1.24 (s, 9H), 1.04 (t, J=7.0 Hz, 3H); LC-MS: m/z 296.2 (M+Na).

Example 18

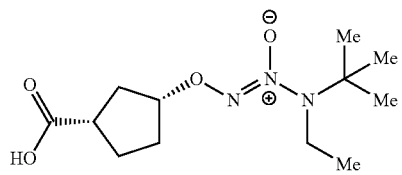 [SMILES: CCN(/[N+]([O-])=N/O[C@@H]1CC[C@H](C(=O)O)C1)C(C)(C)C]

(1S,3R)-3-({[(1Z)-2-tert-butyl-2-ethyl-1-oxido-1λ⁵-diazan-1-ylidene]amino}oxy)cyclopentanecarboxylic acid The title compound was made by following the procedures described in EXAMPLE 17, Step C substituting benzyl (1S, 3R)-3-({[(1Z)-2-tert-butyl-2-ethyl-1-oxido-1λ⁵-diazan-1-ylidene]amino}oxy)cyclopentanecarboxylate for benzyl (1R,3S)-3-({[(1Z)-2-tert-butyl-2-ethyl-1-oxido-1λ⁵-diazan-1-ylidene]amino}oxy)cyclopentanecarboxylate in step E.

Example 19

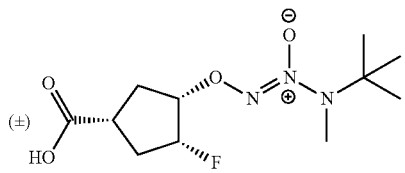 [SMILES: CN(/[N+]([O-])=N/O[C@H]1C[C@@H](C(=O)O)C[C@H]1F)C(C)(C)C]

(1RS,3S,4RS)-3-({[(1Z)-2-tert-butyl-2-methyl-1-oxido-1λ⁵-diazan-1-ylidene]amino}oxy)-4-fluorocyclopentanecarboxylic acid Step A: methyl (3aR,5s,6aS)tetrahydro-3aH-cyclopenta[d][1,3,2]dioxathiole-5-carboxylate 2,2-dioxide To a dichloromethane (100 mL) solution of methyl 3,4-dihydroxycyclopentanecarboxylate (14.7 g, 92.0 mmol) was added thionyl chloride (8.05 mL, 110 mmol) slowly. After 2 hours, the reaction mixture was added to a stirring acetonitrile (100 mL)/water (100 mL) solution of sodium periodate (39.7 g, 185 mmol), followed by ruthenium(IV) oxide hydrate (0.296 g, 1.96 mmol). After 3 hours, the reaction mixture was diluted with water (400 mL) and extracted with diethyl ether (3×400 mL). The combined organic extracts were washed with brine, dried (magnesium sulfate), and concentrated in vacuo to afford a black solid. The residue was purified by column chromatography, eluting with hexanes/ethyl acetate to give the title compound as the less polar fractions. ¹H NMR (500 MHz, CDCl₃) δ 5.38 (d, J=4.7 Hz, 2H), 3.73 (s, 3H), 3.35 (tt, J=11.2, 6.5 Hz, 1H), 2.49 (dd, J=15.3, 6.6 Hz, 2H), 2.19-2.11 (m, 2H).

Step B: methyl (1RS,3RS,4RS)-3-({[(1Z-2-tert-butyl-2-methyl-1-oxido-1λ⁵-diazan-1-ylidene]amino}oxy)-4-hydroxycyclopentanecarboxylate A mixture of methyl (3aR,5s,6aS)tetrahydro-3aH-cyclopenta[d][1,3,2]dioxathiole-5-carboxylate 2,2-dioxide (0.821 g, 3.69 mmol) and sodium 1-(N-tert-butylmethylamino)diazen-1-ium-1,2-diolate (0.812 g, 4.80 mmol) in tetrahydrofuran (15 mL) was heated at 60° C. for 16 hours. Once the reaction solution was cooled to room temperature, 4N aqueous hydrochloric acid in methanol (1.0 mL, 4.0 mmol) was added to the solution and heated at 40° C. for 30 minutes. The solution was diluted with water and extracted with ethyl acetate (3×50 mL). The organics were washed with brine, dried over magnesium sulfate, and concentrated in vacuo. The residue was purified using column chromatography, affording the title compound as a colorless liquid: ¹H NMR (500 MHz, CDCl₃) δ 4.63-4.59 (m, 1H), 4.45-4.42 (m, 1H), 3.69 (s, 3H), 3.09 (quintet, J=8.7 Hz, 1H), 2.80 (s, 3H), 2.56-2.49 (m, 1H), 2.32-2.26 (m, 1H), 2.16-2.11 (m, 1H), 2.00-1.93 (m, 1H), 1.23 (s, 9H).

Step C: methyl (1RS,3S,4RS)-3-({[(1Z)-2-tert-butyl-2-methyl-1-oxido-1λ⁵-diazan-1-ylidene]amino}oxy)-4-fluorocyclopentanecarboxylate To a dichloromethane solution (20 mL) of methyl (1RS,3RS,4RS)-3-({[(1Z)-2-tert-butyl-2-methyl-1-oxido-1λ⁵-diazan-1-ylidene]amino}oxy)-4-hydroxycyclopentane carboxylate (0.882 g, 3.05 mmol) at −78° C. was added bis(2-methoxyethyl)aminosulfur trifluoride (1.5 mL, 3.62 mmol) over 2 minutes. The reaction was stirred at −78° C. for 1 hour and then warmed to −20° C. in a methanol-ice bath. This reaction mixture was then allowed to warm to room temperature over 6 hours and quenched with water. It was extracted with ethyl acetate (3×70 mL), and the combined organic extracts were washed with saturated sodium bicarbonate, brine, and dried over magnesium sulfate. The organics were concentrated in vacuo and purified by column chromatography (ethyl acetate/hexanes), affording the title compound as a colorless liquid. ¹H NMR (500 MHz, CDCl₃) δ 5.06 (dddd, J=53.6, 4.7, 3.6, 2.5 Hz, 1H), 4.60 (dtd, J=19.7, 8.7, 3.6 Hz, 1H), 3.72 (s, 3H), 2.88 (qd, J=9.6, 6.1 Hz, 1H), 2.82 (s, 3H), 2.49-2.38 (m, 3H), 2.23 (dddd, J=32.7, 15.4, 10.5, 4.8 Hz, 1H), 1.24 (s, 9H).

Step D: (1RS,3S,4RS)-3-({[(1Z)-2-tert-butyl-2-methyl-1-oxido-1λ⁵-diazan-1-ylidene]amino}oxy)-4-fluorocyclopentanecarboxylic acid The title compound was made by following the procedures described in EXAMPLE 1, Step D substituting methyl (1RS,3S,4RS)-3-({[(1Z)-2-tert-butyl-2-methyl-1-oxido-1λ⁵-diazan-1-ylidene]amino}oxy)-4-fluorocyclopentanecarboxylate for ethyl (1S,3S)-3-({[(1Z)-2-tert-butyl-2-ethyl-1-oxido-1λ⁵-diazan-1-ylidene]amino}oxy)cyclopentane carboxylate. ¹H NMR (500 MHz, CDCl₃) δ 5.07 (ddt, J=53.4, 4.7, 3.1 Hz, 1H), 4.63 (dtd, J=19.0, 8.4, 3.4 Hz, 1H), 2.93 (qd, J=9.4, 5.6 Hz, 1H), 2.81 (s, 3H), 2.58-2.38 (m, 3H), 2.37-2.21 (m, 1H), 1.23 (s, 9H); LC-MS: m/z 299.9 (M+Na).

Example 20

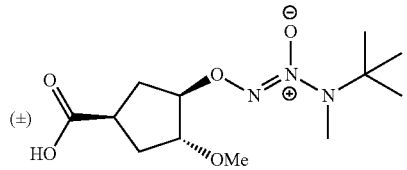 [SMILES: CO[C@@H]1C[C@@H](C(=O)O)C[C@H]1O/N=[N+](\[O-])N(C)C(C)(C)C]

(1RS,3RS,4RS)-3-({[(1Z)-2-tert-butyl-2-methyl-1-oxido-1λ⁵-diazan-1-ylidene]amino}oxy)-4-methoxycyclopentanecarboxylic acid Step A: methyl (1RS,3RS,4RS)-3-({[(1Z)-2-tert-butyl-2-methyl-1-oxido-1λ⁵-diazan-1-ylidene]amino}oxy)-4-methoxycyclopentanecarboxylate To a chloroform (10 mL) solution of methyl (1RS,3RS,4RS)-3-({[(1Z)-2-tert-butyl-2-methyl-1-oxidohydrazono]amino}oxy)-4-hydroxycyclopentanecarboxylate (EXAMPLE 19, Step B, 451 mg, 1.56 mmol) was added 1,8-bis(dimethylamino)naphthalene (717 mg, 3.34 mmol), followed by trimethyloxonium tetrafluoroborate (478 mg, 3.23 mmol). After 64 hours, the reaction mixture was concentrated in vacuo, and the residue was purified by column chromatography, eluting with hexanes/ethyl acetate to give the title compound as a yellow liquid. ¹H NMR (500 MHz, CDCl₃) δ 4.71 (ddd, J=6.8, 5.2, 2.2 Hz, 1H), 3.94 (dt, J=6.0, 2.4 Hz, 1H); 3.68 (s, 3H), 3.35 (s, 3H), 3.00 (quintet, J=8.7 Hz, 1H), 2.81

(s, 3H), 2.47 (dt, J=14.4, 7.7 Hz, 1H), 2.24-2.10 (m, 2H), 2.04 (ddd, J=13.9, 7.8, 2.4 Hz, 1H), 1.24 (s, 9H).

Step B: (1RS,3RS,4RS)-3-({[(1Z)-2-tert-butyl-2-methyl-1-oxido-1λ⁵-diazan-1-ylidene]amino}oxy)-4-methoxycyclopentanecarboxylic acid The title compound was made by following the procedures described in step D, EXAMPLE 1 substituting methyl (1RS,3RS,4RS)-3-({[(1Z)-2-tert-butyl-2-methyl-1-oxido-1λ⁵-diazan-1-ylidene]amino}oxy)-4-methoxycyclopentanecarboxylate for ethyl (1S,3S)-3-({[(1Z)-2-tert-butyl-2-ethyl-1-oxido-1λ⁵-diazan-1-ylidene]amino}oxy)cyclopentanecarboxylate. ¹H NMR (500 MHz, CDCl₃) δ 4.73 (td, J=5.7, 1.9 Hz, 1H), 3.97-3.93 (m, 1H), 3.36 (s, 3H), 3.04 (quintet, J=8.7 Hz, 1H), 2.80 (s, 3H), 2.54-2.44 (m, 1H), 2.24-2.13 (m, 2H), 2.10-2.05 (m, 1H), 1.23 (s, 9H); LC-MS: m/z 312.2 (M+Na).

Example 21

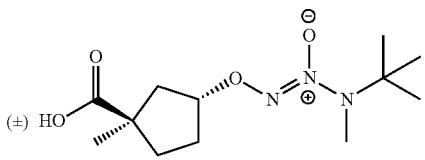 [SMILES: CN(/[N+]([O-])=N/O[C@@H]1CC[C@@](C)(C(=O)O)C1)C(C)(C)C]

(1RS,3RS)-3-({[(1Z)-2-tert-butyl-2-methyl-1-oxido-1λ⁵-diazan-1-ylidene]amino}oxy)-1-methylcyclopentanecarboxylic acid Step A: methyl (1RS,3RS)-3-({[(1Z)-2-tert-butyl-2-methyl-1-oxido-1λ⁵-diazan-1-ylidene]amino}oxy)-1-methylcyclopentanecarboxylate Methyl iodide (0.40 mL, 6.4 mmol) was added to a tetrahydrofuran solution (20 mL) of lithium diisopropylamide (1.50 mL, 3.00 mmol) and methyl (1R,3S)-3-({[(1Z)-2-tert-butyl-2-methyl-1-oxido-1λ⁵-diazan-1-ylidene]amino}oxy)cyclopentanecarboxylate (0.525 g, 1.92 mmol) at −78° C. The solution was gradually warmed to room temperature over 16 hours. It was then quenched with 1N hydrochloric acid and extracted with ethyl acetate (3×30 mL). The organics were concentrated in vacuo and purified by column chromatography (hexanes/ethyl acetate), affording the (1RS,3RS) diastereomer of the title compound as the less polar fractions and the (1RS,3SR) diastereomer as the more polar fractions. (1RS,3RS) diastereomer: ¹H NMR (500 MHz, CDCl₃) δ 4.94 (dt, J=11.0, 4.2 Hz, 1H), 3.68 (s, 3H), 2.81 (s, 3H), 2.63 (dd, J=14.6, 6.8 Hz, 1H), 2.18-2.09 (m, 1H), 2.08-2.01 (m, 2H), 1.82 (dd, J=14.6, 3.8 Hz, 1H), 1.76 (dt, J=12.8, 8.6 Hz, 1H), 1.37 (s, 3H), 1.24 (s, 9H). (1RS,3SR) diastereomer: ¹H NMR (500 MHz, CDCl₃) δ 4.94-4.83 (m, 1H), 3.68 (s, 3H), 2.80 (s, 3H), 2.54 (dd, J=14.4, 3.9 Hz, 1H), 2.41 (dt, J=13.1, 8.1 Hz, 1H), 2.18-2.01 (m, 2H), 1.92 (dd, J=14.4, 6.4 Hz, 1H), 1.53 (ddd, J=13.1, 8.3, 5.8 Hz, 1H), 1.24 (s, 9H).

Step B: (1RS,3RS)-3-({[(1Z)-2-tert-butyl-2-ethyl-1-oxido-1λ⁵-diazan-1-ylidene]amino}oxy-1-methylcyclopentanecarboxylic acid The title compound was made by following the procedures described in step D, EXAMPLE 1 substituting methyl (1RS,3RS)-3-({[(1Z)-2-tert-butyl-2-methyl-1-oxido-1λ⁵-diazan-1-ylidene]amino}oxy)-1-methylcyclopentanecarboxylate for ethyl (1S,3S)-3-({[(1Z)-2-tert-butyl-2-ethyl-1-oxido-1λ⁵-diazan-1-ylidene]amino}oxy)cyclopentanecarboxylate. ¹H NMR (500 MHz, CDCl₃) δ 4.98-4.92 (m, 1H), 2.81 (s, 3H), 2.65 (dd, J=14.7, 6.7 Hz, 1H), 2.19 (ddd, J=12.8, 7.1, 5.3 Hz, 1H), 2.11-2.05 (m, 2H), 1.85 (dd, J=14.6, 3.7 Hz, 1H), 1.80 (dt, J=12.9, 8.7 Hz, 1H), 1.40 (s, 3H), 1.23 (s, 9H); LC-MS: m/z 274.3 (M+H).

Example 22

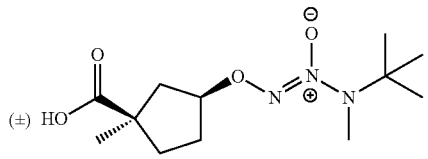 [SMILES: CN(/[N+]([O-])=N/O[C@H]1CC[C@@](C)(C(=O)O)C1)C(C)(C)C]

(1RS,3SR)-3-({[(1Z)-2-tert-butyl-2-ethyl-1-oxido-1λ⁵-diazan-1-ylidene]amino}oxy)-1-methylcyclopentanecarboxylic acid The title compound was made by following the procedures described in EXAMPLE 21 substituting methyl (1RS,3SR)-3-({[(1Z)-2-tert-butyl-2-methyl-1-oxido-1λ⁵-diazan-1-ylidene]amino}oxy)-1-methylcyclopentanecarboxylate for methyl (1RS,3RS)-3-({[(1Z)-2-tert-butyl-2-methyl-1-oxido-1λ⁵-diazan-1-ylidene]amino}oxy)-1-methylcyclopentane carboxylate in step B. ¹H NMR (500 MHz, CDCl₃) δ 4.94-4.89 (m, 1H), 2.80 (s, 3H), 2.59 (dd, J=14.6, 3.2 Hz, 1H), 2.45 (dt, J=13.2, 8.1 Hz, 1H), 2.15-2.05 (m, 2H), 1.90 (dd, J=14.6, 6.1 Hz, 1H), 1.56 (ddd, J=13.3, 8.3, 5.9 Hz, 1H), 1.33 (s, 3H), 1.22 (s, 9H); LC-MS: m/z 274.3 (M+H).

Tables 1-5 describe additional examples of compounds within the scope of the invention:

TABLE 1

| Ex | $R^a$ | $R^2$ |
|---|---|---|
| 23 | —O—N=N⁺(O⁻)N(CH₃)C(CH₃)₃ | —C₆H₄—C(O)OCH₂CH₃ |

TABLE 1-continued $$R^2-\text{cyclopentane}-R^a$$

| Ex | $R^a$ | $R^2$ |
|---|---|---|
| 24 | —O—N=N$^+$(O$^-$)N(CH$_3$)C(CH$_3$)$_3$ | –C$_6$H$_4$–C(O)OH (para) |
| 25 | ⋯O—N=N$^+$(O$^-$)N(CH(CH$_3$)$_2$(CH$_2$-C$_6$H$_5$)) | ⋯C(O)OH |
| 26 | ⋯O—N=N$^+$(O$^-$)N(CH$_2$CH$_3$)C(CH$_3$)$_3$ | –C(O)OH |
| 27 | ⋯O—N=N$^+$(O$^-$)N(CH$_2$CH$_3$)C(CH$_3$)$_3$ | ◂C(O)OCH$_3$ |
| 28 | ◂O—N=N$^+$(O$^-$)N(CH$_2$CH$_3$)C(CH$_3$)$_3$ | ◂C(O)OCH$_3$ |
| 29 | ⋯O—N=N$^+$(O$^-$)N(CH$_3$)C(CH$_3$)$_3$ | ◂CH$_2$OH |
| 30 | ◂O—N=N$^+$(O$^-$)N(CH$_3$)C(CH$_3$)$_3$ | ◂CH$_2$OH |
| 31 | ⋯O—N=N$^+$(O$^-$)N(CH$_2$CH$_3$)C(CH$_3$)$_3$ | ⋯C(O)OCH$_3$ |
| 32 | ◂O—N=N$^+$(O$^-$)N(CH$_2$CH$_3$)C(CH$_3$)$_3$ | ◂CH$_2$OH |
| 33 | ◂O—N=N$^+$(O$^-$)N(CH$_2$CH$_3$)C(CH$_3$)$_3$ | ◂C(O)OH |
| 34 | ⋯O—N=N$^+$(O$^-$)N(CH$_2$CH$_3$)C(CH$_3$)$_3$ | ⋯C(O)OH |
| 35 | ⋯O—N=N$^+$(O$^-$)N(CH$_2$CH$_3$)C(CH$_3$)$_3$ | ◂C(O)OH |
| 36 | ◂O—N=N$^+$(O$^-$)N(CH$_2$CH$_3$)C(CH$_3$)$_3$ | ◂C(O)O–C$_6$H$_5$ |

TABLE 1-continued $R^2$—[cyclopentane]—$R^a$

| Ex | $R^a$ | $R^2$ |
|---|---|---|
| 37 | —O—N=N$^+$(O$^-$)N(CH$_2$CH$_3$)C(CH$_3$)$_3$ | —C(O)OCH$_2$—C$_6$H$_5$ |
| 38 | —O—N=N$^+$(O$^-$)N(CH$_3$)C(CH$_3$)$_3$ | —C(O)OCH$_2$CH$_2$N$^+$(CH$_3$)$_3$ |
| 39 | ⋯O—N=N$^+$(O$^-$)N(CH$_2$CH$_3$)C(CH$_3$)$_3$ | —C(O)OCH$_2$—C$_6$H$_5$ |
| 40 | —O—N=N$^+$(O$^-$)N(CH$_2$CH$_3$)C(CH$_3$)$_3$ | —C(O)OCH$_2$CH$_3$ |
| 41 | —O—N=N$^+$(O$^-$)N(CH$_2$CH$_3$)C(CH$_3$)$_3$ | —C$_6$H$_4$—OCH$_3$ |
| 42 | ⋯O—N=N$^+$(O$^-$)N(CH$_2$CH$_3$)C(CH$_3$)$_3$ | ⋯C(O)OCH$_2$—C$_6$H$_5$ |
| 43 | —O—N=N$^+$(O$^-$)N((CH$_2$)$_2$(CH$_3$)$_2$)C(CH$_3$)$_3$ | —C(O)OH |
| 44 | —O—N=N$^+$(O$^-$)N(CH$_2$CH$_3$)C(CH$_3$)$_3$ | —C$_6$H$_4$—OCH$_3$ |
| 45 | —O—N=N$^+$(O$^-$)N((CH$_2$)$_3$CH$_3$)C(CH$_3$)$_3$ | —C$_6$H$_4$—OCH$_3$ |
| 46 | —O—N=N$^+$(O$^-$)N((CH$_2$)$_3$CH$_3$)C(CH$_3$)$_3$ | —C(O)OH |
| 47 | ⋯O—N=N$^+$(O$^-$)N((CH$_2$)$_2$OH)C(CH$_3$)$_3$ | —C$_6$H$_4$—OCH$_3$ |
| 48 | ⋯O—N=N$^+$(O$^-$)N((CH$_2$)$_3$CH$_3$)C(CH$_3$)$_3$ | ⋯C$_6$H$_4$—OCH$_3$ |
| 49 | ⋯O—N=N$^+$(O$^-$)N((CH$_2$)$_2$CH$_3$)C(CH$_3$)$_3$ | ⋯C$_6$H$_4$—OCH$_3$ |

TABLE 1-continued

Structure: cyclopentane with R² and Rᵃ substituents

| Ex | Rᵃ | R² |
|---|---|---|
| 50 | ⋯O—N=N⁺(O⁻)N(CH₃)C(CH₃)₃ | —C₆H₄—OCH₃ (para) |
| 51 | ◂O—N=N⁺(O⁻)N((CH₂)₂CH₃)C(CH₃)₃ | —C₆H₄—OCH₃ (para) |
| 52 | ⋯O—N=N⁺(O⁻)N(CH₃)C(CH₃)₃ | ⋯C(O)OH |
| 53 | ⋯O—N=N⁺(O⁻)N((CH₂)₂CH₃)C(CH₃)₃ | ⋯C(O)OH |
| 54 | ⋯O—N=N⁺(O⁻)N((CH₂)₃CH₃)C(CH₃)₃ | ⋯C(O)OH |
| 55 | ◂O—N=N⁺(O⁻)N((CH₂)₂N₃)C(CH₃)₃ | —C₆H₄—OCH₃ (para) |
| 56 | ◂O—N=N⁺(O⁻)N((CH₂)₂CH₃)C(CH₃)₃ | ◂C(O)OH |
| 57 | —O—N=N⁺(O⁻)N(CH₃)C(CH₃)₃ | —P(O)(OCH₂CH₃)₂ |

TABLE 2

Structure: cyclopentane with Rᵃ, R¹, and R² substituents

| Ex | Rᵃ | R¹ | R² |
|---|---|---|---|
| 58 | —O—N=N⁺(O⁻)N(CH₃)C(CH₃)₃ | ⋯OH | —C(O)OCH₃ |
| 59 | —O—N=N⁺(O⁻)N(CH₃)C(CH₃)₃ | ⋯OCH₃ | —C(O)OCH₃ |
| 60 | —O—N=N⁺(O⁻)N(CH₃)C(CH₃)₃ | =O | —C(O)OCH₃ |
| 61 | ◂O—N=N⁺(O⁻)N(CH₃)C(CH₃)₃ | ◂F | ◂C(O)OCH₃ |
| 62 | ◂O—N=N⁺(O⁻)N(CH₃)C(CH₃)₃ | ◂F | ◂C(O)OH |

TABLE 3

[Structure: cyclopentane with R⁴ and Rᵃ substituents]

| Ex | Rᵃ | R⁴ |
|---|---|---|
| 63 | ◀O—N=N⁺(O⁻)N(CH₃)C(CH₃)₃ | ⦙OH |
| 64 | ◀O—N=N⁺(O⁻)N(CH₃)C(CH₃)₃ | ⦙C(O)OCH₂CH₃ |

TABLE 4

[Structure: cyclopentane with Rᵃ, R², R³ substituents]

| Ex | Rᵃ | R² | R³ |
|---|---|---|---|
| 65 | ⦙O—N=N⁺(O⁻)N(CH₃)C(CH₃)₃ | C(O)OCH₃ | ⦙CH₃ |
| 66 | ⦙O—N=N⁺(O⁻)N(CH₃)C(CH₃)₃ | ⦙C(O)OCH₃ | ◀CH₃ |
| 67 | ⦙O—N=N⁺(O⁻)N(CH₃)C(CH₃)₃ | ◀C(O)OH | ⦙CH₃ |
| 68 | ⦙O—N=N⁺(O⁻)N(CH₃)C(CH₃)₃ | ⦙C(O)OH | ◀CH₃ |
| 69 | ⦙O—N=N⁺(O⁻)N(CH₂CH₃)C(CH₃)₃ | ◀C(O)OCH₃ | ⦙CH₃ |
| 70 | ◀O—N=N⁺(O⁻)N(CH₂CH₃)C(CH₃)₃ | ◀C(O)OCH₃ | ⦙CH₃ |
| 71 | ⦙O—N=N⁺(O⁻)N(CH₂CH₃)C(CH₃)₃ | ◀C(O)OH | ⦙CH₃ |

TABLE 5

[Structure: cyclopentane with R⁵, Rᵃ, R² substituents]

| Ex | Rᵃ | R² | R⁵ |
|---|---|---|---|
| 72 | ⦙O—N=N⁺(O⁻)N(CH₂CH₃)C(CH₃)₃ | ⦙C(O)OH | ◀D |
| 73 | ⦙O—N=N⁺(O⁻)N(CH₂CH₃)C(CH₃)₃ | ◀C(O)OH | ⦙D |

Compounds of the invention were evaluated for blood pressure reduction efficacy using the following canine telemetry protocol described below.

Male beagle dogs (approximately 1-3 years old) with a body weight of between 10 and 16 kg were surgically implanted with DSI radiotelemetry devices (model: TL11M2-D70-PCT). Briefly, under an inhalant anesthesia, isoflurane/oxygen mixture (1-3.5%/to effect), the body of the telemetry device was positioned and secured intra-abdominally. Subsequently, the arterial catheter of the telemetry device was passed subcutaneously to the inguinal area and introduced into the femoral artery and advanced to the level of the descending aorta. The catheter was secured with 2-0 silk ligatures. The muscle and underlying fascia was closed over the catheter using absorbable suture and the skin was closed using non-absorbable suture. The animals were allowed a minimum recovery period of 2 weeks between surgery and the evaluation of test compounds.

Compound evaluation consisted of a 3 day paradigm at a 3 mg/kg dose. On the first day, no compounds were administered during a 24 hour period of baseline data collection. Blood pressure and heart rate data were collected continuously for one minute periods at 10 minute intervals. On the days of compound administration half the animals received test article with the other half receiving the vehicle used for compound formulation. All test materials were administered by oral gavage in a volume of 1 mL/kg. Data are expressed either as raw values (mm Hg or beats per minute) or as the change from baseline (average value for about 12 hours in low activity period prior to dosing). Change is SBP (systolic blood pressure) and PP (pulse pressure) over time is shown below:

| | ΔSBP (mm Hg) | | | ΔPP (mm Hg) | | |
|---|---|---|---|---|---|---|
| Example | 1-6 h | 6-12 h | 12-18 h | 1-6 h | 6-12 h | 12-18 h |
| 1 | −12 | −9 | −7 | −7 | −7 | −5 |
| 7 | −9 | −11 | −10 | −4 | −9 | −8 |
| 18 | −18 | −10 | −4 | −14 | −10 | −6 |

What is claimed is:

1. A compound having the formula I:

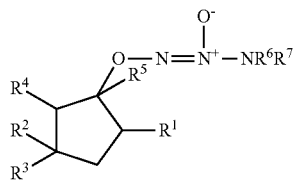

or a pharmaceutically acceptable salt thereof, wherein $R^1$ is hydrogen, —OH, —O—$C_{1-6}$ alkyl, =O, or halogen;

$R^2$ is
  hydrogen,
  —C(O)O$R^8$,
  —$C_6H_5$C(O)O$R^8$,
  —(CH$_2$)$_{1-2}$OH,
  —CR$^9$R$^{10}$OH,
  —C(O)O(CH$_2$)$_{0-2}$ aryl,
  —C(O)NR$^9$R$^{10}$,
  —C(O)SO$_2$NR$^9$R$^{10}$,
  —$C_6H_5$OR$^9$,
  —W—C(O)OR$^8$,
  —W—OR$^9$,
  —Y, or
  —P(O)(OR$^9$)(OR$^{10}$);

$R^3$ is hydrogen or —$C_{1-6}$ alkyl;

$R^4$ is hydrogen, —OH, or —C(O)OR$^9$;

$R^5$ is hydrogen or deuterium;

$R^6$ and $R^7$ are independently —$C_{1-6}$ alkyl, fluoro-substituted-$C_{1-6}$ alkyl, deutero-substituted —$C_{1-6}$ alkyl or —(CH$_2$)$_{1-2}$R$^{11}$, wherein any carbon atom of the fluoro-substituted —$C_{1-6}$ alkyl is mono- or di-substituted with fluoro, and any carbon atom of the deutero-substituted —$C_{1-6}$ alkyl is mono- or di-substituted with fluoro;

$R^8$, in each instance in which it occurs, hydrogen, —$C_{1-6}$ alkyl, or —(CH$_2$)$_2$N$^+$(CH$_3$)$_3$;

$R^9$ and $R^{10}$, in each instance in which they occur, are independently —$C_{1-6}$ alkyl;

$R^{11}$ is —OH, —O—$C_{1-6}$ alkyl, —OCD3, —OC(O)OC$_{1-6}$ alkyl, —NH$_2$, —$C_6H_5$, —N$_3$, or W;

W is an unsubstituted 5- or 6-membered heteroaryl ring having 1, 2, or 3 nitrogen atoms, or a substituted 5- or 6-membered heteroaryl ring having 1, 2, or 3 nitrogen atoms that is mono- or di-substituted at any carbon atom with $R^6$ or $R^7$;

Y is a 5- or 6-membered heterocyclic ring having 1, 2, 3 or 4 heteroatoms which are N, O or S, or stereoisomers thereof, or pharmaceutically acceptable salts thereof, or pharmaceutically acceptable salts of stereoisomers thereof.

2. A compound of claim 1, wherein the compound has the formula Ia:

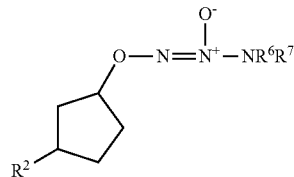

or a pharmaceutically acceptable salt thereof.

3. A compound of claim 1, wherein $R^1$ is hydrogen, —OH, —OCH$_3$, =O, or F, or a pharmaceutically acceptable salt thereof.

4. A compound of claim 1, wherein $R^2$ is
  —C(O)OR$^8$,
  —$C_6H_5$C(O)OR$^8$,
  —(CH$_2$)$_{1-2}$OH,
  —C(O)O(CH$_2$)$_{0-2}$ aryl,
  —$C_6H_5$OR$^9$, or
  —P(O)(OR$^9$)(OR$^{10}$), or a pharmaceutically acceptable salt thereof.

5. A compound of claim 4, wherein $R^2$ is
  —C(O)OH,
  —C(O)OCH$_3$,
  —C(O)OCH$_2$CH$_3$,
  —C(O)OC$_6$H$_5$,
  —C(O)OCH$_2$CH$_2$N(CH$_3$)$_3$,
  —$C_6H_5$C(O)OCH$_2$CH$_3$,
  —$C_6H_5$C(O)OH,
  —CH$_2$OH,
  —C(O)OCH$_2$C$_6$H$_5$,
  —$C_6H_5$OCH$_3$, or
  —P(O)(OCH$_2$CH$_3$)$_2$ or a pharmaceutically acceptable salt thereof.

6. A compound of claim 4, wherein $R^3$ is hydrogen or —CH$_3$, or a pharmaceutically acceptable salt thereof.

7. A compound of claim 6, wherein $R^3$ is hydrogen, or a pharmaceutically acceptable salt thereof.

8. A compound of claim 7, wherein $R^4$ is hydrogen, —OH, or —C(O)OCH$_2$CH$_3$, or a pharmaceutically acceptable salt thereof.

9. A compound of claim 8, wherein $R^4$ is hydrogen, or a pharmaceutically acceptable salt thereof.

10. A compound of claim 1, wherein $R^5$ is hydrogen, or a pharmaceutically acceptable salt thereof.

11. A compound of claim 1, wherein $R^6$ is
  —CH$_3$,
  —CH(CH$_3$)$_2$,
  —CH$_2$CH$_3$,
  —(CH$_2$)$_3$CH$_3$,
  —(CH$_2$)$_2$CH(CH$_3$)$_2$,
  —(CH$_2$)$_2$OH,
  —(CH$_2$)$_2$OCH$_3$,
  —(CH$_2$)$_2$OCD$_3$,
  —(CH$_2$)$_2$OC(O)OC(CH$_3$)$_3$,
  —NH$_2$
  —CH$_2$CH$_2$CH$_3$,
  —CH$_2$CH$_2$N$^+$$_3$, or

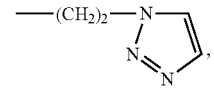

or a pharmaceutically acceptable salt thereof.

12. A compound of claim 1, wherein R⁷ is —C(CH₃)₃ or —CH₂C₆H₅, or a pharmaceutically acceptable salt thereof.

13. A compound of claim 12, wherein R⁷ is —C(CH₃)₃, or a pharmaceutically acceptable salt thereof.

14. A compound of claim 1, which is (1R,3R)-3-({[(1Z)-2-tert-butyl-2-ethyl-1-oxido-1λ⁵-diazan-1-ylidene]amino}oxy)cyclopentanecarboxylic acid, ethyl (1R,3R)-3-({[(1Z)-2-tert-butyl-2-ethyl-1-oxido-1λ⁵-diazan-1-ylidene]amino}oxy)cyclopentanecarboxylate, (1S,3S)-3-({[(1Z)-2-tert-butyl-2-ethyl-1-oxido-1λ⁵-diazan-1-ylidene]amino}oxy)cyclopentanecarboxylic acid, (1R,3R)-3-({[(1Z)-2-tert-butyl-2-methyl-1-oxido-1λ⁵-diazan-1-ylidene]amino}oxy)cyclopentanecarboxylic acid, (1S,3S)-3-({[(1Z)-2-tert-butyl-2-methyl-1-oxido-1λ⁵-diazan-1-ylidene]amino}oxy)cyclopentanecarboxylic acid, (1R,3R)-3-({[(1Z)-2-tert-butyl-2-(2-methoxyethyl)-1-oxido-1λ⁵-diazan-1-ylidene]amino}oxy)cyclopentanecarboxylic acid, 2-{tert-butyl[(Z)-{[(1R,3R)-3-(4-methoxyphenyl)cyclopentyl]oxy}-NNO-azoxy]amino}ethanol, N-(2-methoxyethyl)-N—[(Z)-{[(1R,3R)-3-(4-methoxyphenyl)cyclopentyl]oxy}-NNO-azoxy]-2-methylpropan-2-amine, (1R,3R)-3-({[(1Z)-2-tert-butyl-2-{2-[(²H₃)methyloxy]ethyl}-1-oxido-1λ⁵-diazan-1-ylidene]amino}oxy)cyclopentanecarboxylic acid, (1R,3R)-3-({[(1Z)-2-tert-butyl-2-propyl-1-oxido-1λ⁵-diazan-1-ylidene]amino}oxy)cyclopentanecarboxylic acid, (1R,3R)-3-({[(1Z)-2-tert-butyl-2-butyl-1-oxido-1λ⁵-diazan-1-ylidene]amino}oxy)cyclopentanecarboxylic acid, (1R,3R)-3-({[(1Z)-2-tert-butyl-2-(3-methylbutyl)-1-oxido-1λ⁵-diazan-1-ylidene]amino}oxy)cyclopentanecarboxylic acid, (1S,3R)-3-({[(1Z)-2-tert-butyl-2-methyl-1-oxido-1λ⁵-diazan-1-ylidene]amino}oxy)cyclopentanecarboxylic acid, (1S,3R)-3-({[(1Z)-2-tert-butyl-2-propyl-1-oxido-1λ⁵-diazan-1-ylidene]amino}oxy)cyclopentanecarboxylic acid, (1S,3R)-3-({[(1Z)-2-tert-butyl-2-butyl-1-oxido-1λ⁵-diazan-1-ylidene]amino}oxy)cyclopentanecarboxylic acid, (1S,3R)-3-({[(1Z)-2-tert-butyl-2-(2-methoxyethyl)-1-oxido-1λ⁵-diazan-1-ylidene]amino}oxy)cyclopentanecarboxylic acid, (1S,3R)-3-({[(1Z)-2-{2-[(tert-butoxycarbonyl)oxy]ethyl}-2-tert-butyl-1-oxido-1λ⁵-diazan-1-ylidene]amino}oxy)cyclopentanecarboxylic acid, (1S,3R)-3-({[(1Z)-2-(2-aminoethyl)-2-tert-butyl-1-oxido-1λ⁵-diazan-1-ylidene]amino}oxy)cyclopentanecarboxylic acid, (1S,3R)-3-[({(1Z)-2-tert-butyl-1-oxido-2-[2-(1H-1,2,3-triazol-1-yl)ethyl]-1λ⁵-diazan-1-ylidene}amino)oxy]cyclopentanecarboxylic acid, (1R,3S)-3-({[(1Z)-2-tert-butyl-2-ethyl-1-oxido-1λ⁵-diazan-1-ylidene]amino}oxy)cyclopentanecarboxylic acid, (1S,3R)-3-({[(1Z)-2-tert-butyl-2-ethyl-1-oxido-1λ⁵-diazan-1-ylidene]amino}oxy)cyclopentanecarboxylic acid, (1RS,3SR,4RS)-3-({[(1Z)-2-tert-butyl-2-methyl-1-oxido-1λ⁵-diazan-1-ylidene]amino}oxy)-4-fluorocyclopentanecarboxylic acid, (1RS,3RS,4RS)-3-({[(1Z)-2-tert-butyl-2-methyl-1-oxido-1λ⁵-diazan-1-ylidene]amino}oxy)-4-methoxycyclopentanecarboxylic acid, (1RS,3RS)-3-({[(1Z)-2-tert-butyl-2-methyl-1-oxido-1λ⁵-diazan-1-ylidene]amino}oxy)-1-methylcyclopentanecarboxylic acid, and (1RS,3SR)-3-({[(1Z)-2-tert-butyl-2-ethyl-1-oxido-1λ⁵-diazan-1-ylidene]amino}oxy)-1-methylcyclopentanecarboxylic acid, or a pharmaceutically acceptable salt thereof.

15. A pharmaceutical composition comprising a compound of claim 1, or a pharmaceutically acceptable salt thereof, and a pharmaceutically acceptable carrier.

16. A pharmaceutical composition comprising a compound of claim 14, or a pharmaceutically acceptable salt thereof, and a pharmaceutically acceptable carrier.

17. A pharmaceutical composition comprising a compound of claim 1, or a pharmaceutically acceptable salt thereof, a diuretic, and a pharmaceutically acceptable carrier.

18. A method for treating hypertension in a patient which comprises administering to the patient a therapeutically effective amount of the composition of claim 15.

* * * * *

UNITED STATES PATENT AND TRADEMARK OFFICE
CERTIFICATE OF CORRECTION

| | |
|---|---|
| PATENT NO. | : 8,648,058 B2 |
| APPLICATION NO. | : 13/577797 |
| DATED | : February 11, 2014 |
| INVENTOR(S) | : Amjad Ali et al. |

It is certified that error appears in the above-identified patent and that said Letters Patent is hereby corrected as shown below:

On the title page, col. 2, under abstract delete "18 Claims, 13 Drawing Sheets" and insert
--18 Claims, No Drawing Sheets--.

Figure 1B:
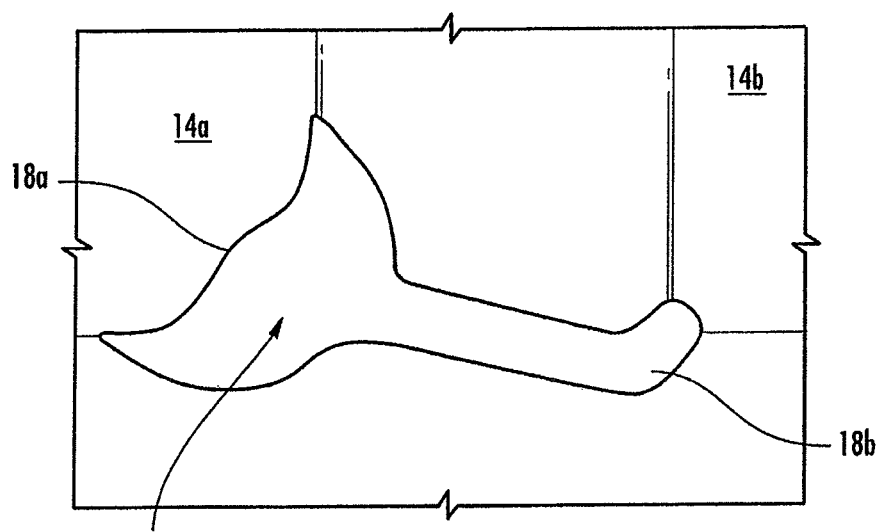
Figure 1C:
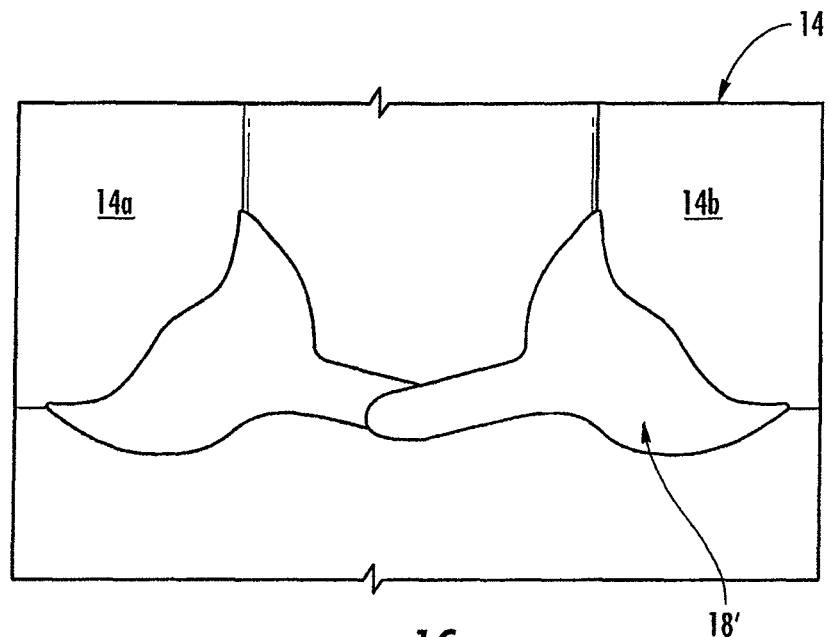
Figure 2A:
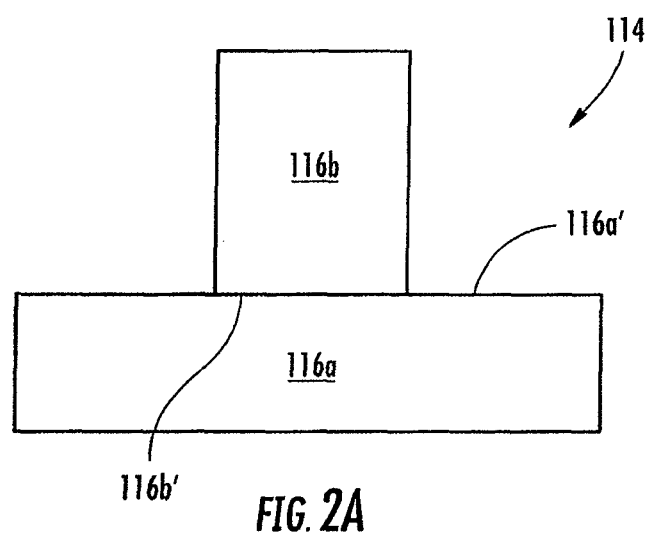
Figure 2B:
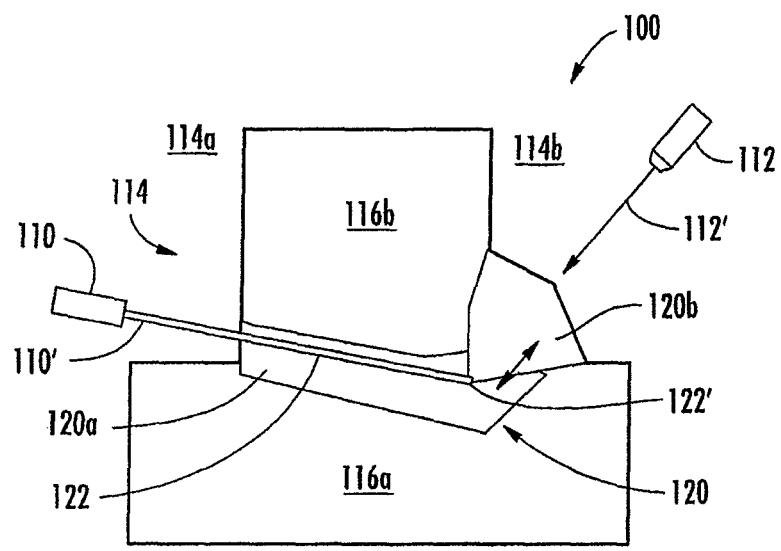
Figure 2C:
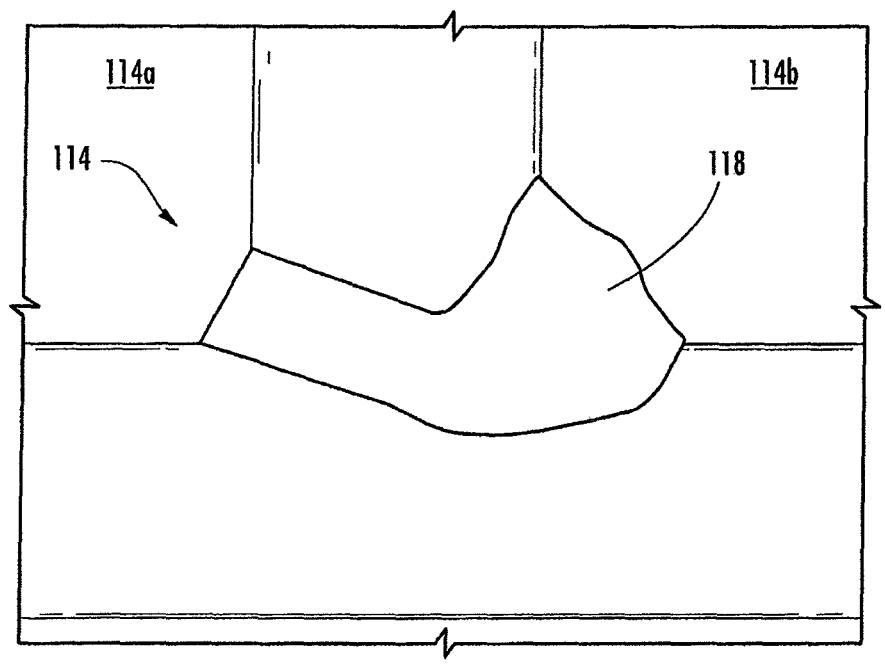
Figure 3A:
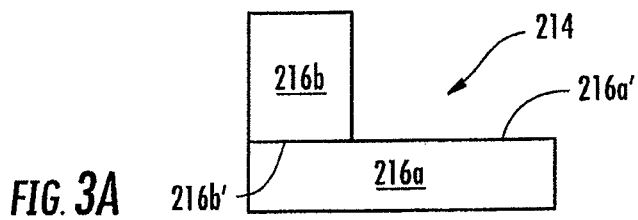
Figure 3B:
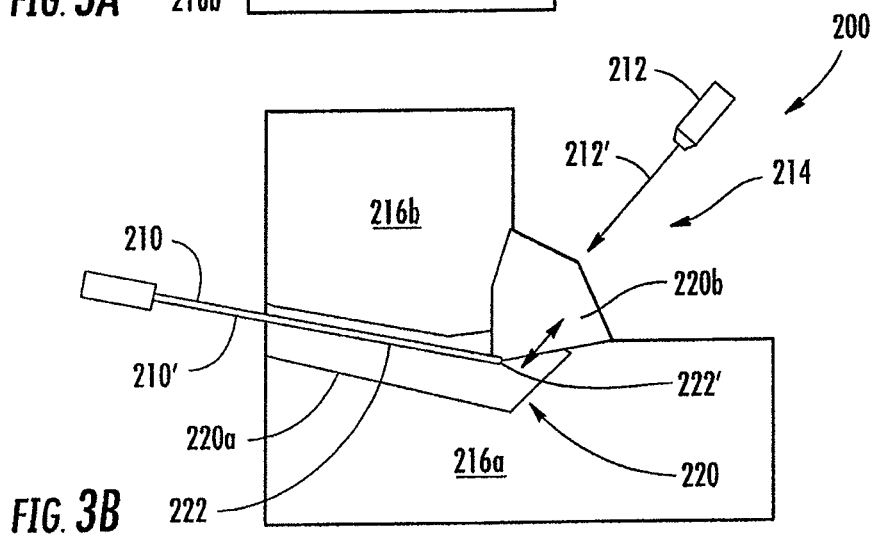
Figure 4A:
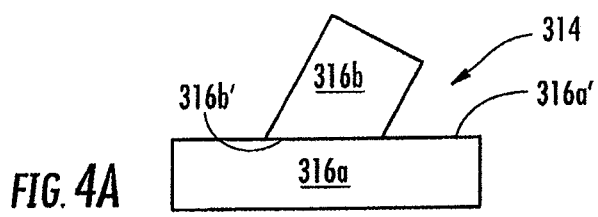
Figure 4B:
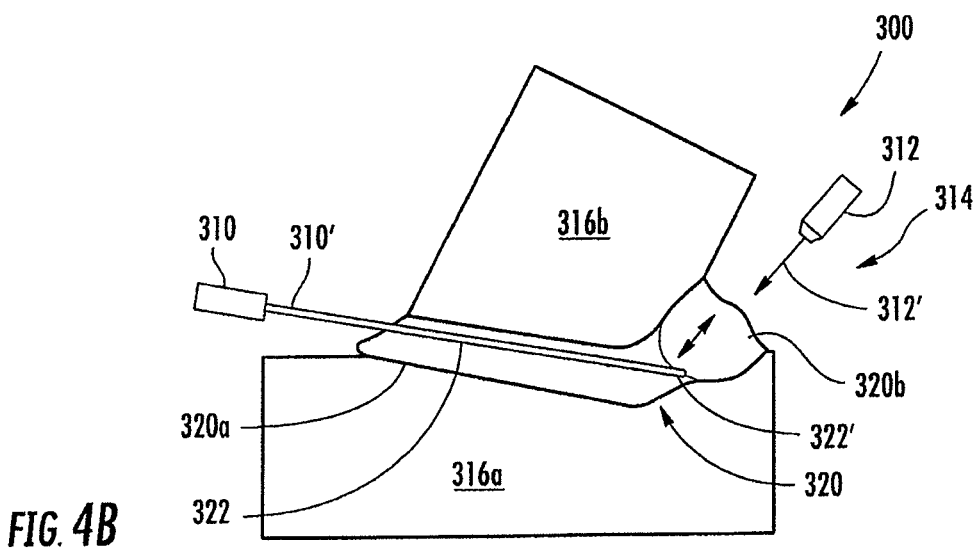
Figure 5A:
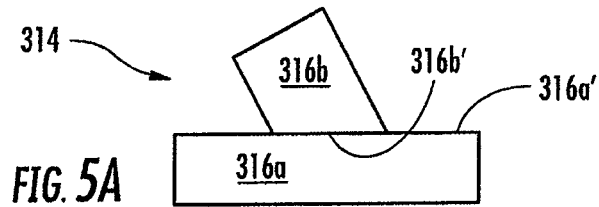
Figure 5B:
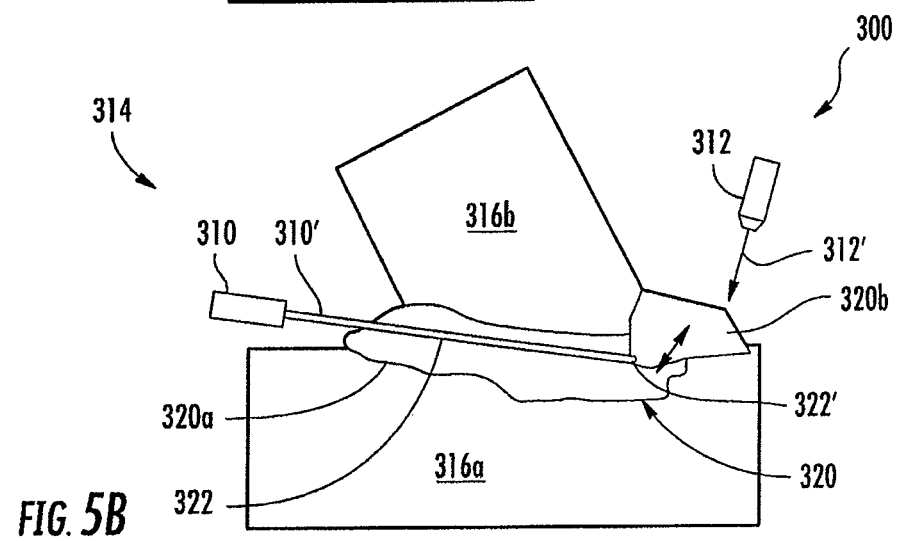
Figure 6A:
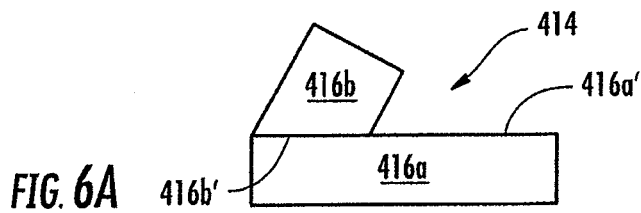
Figure 6B:
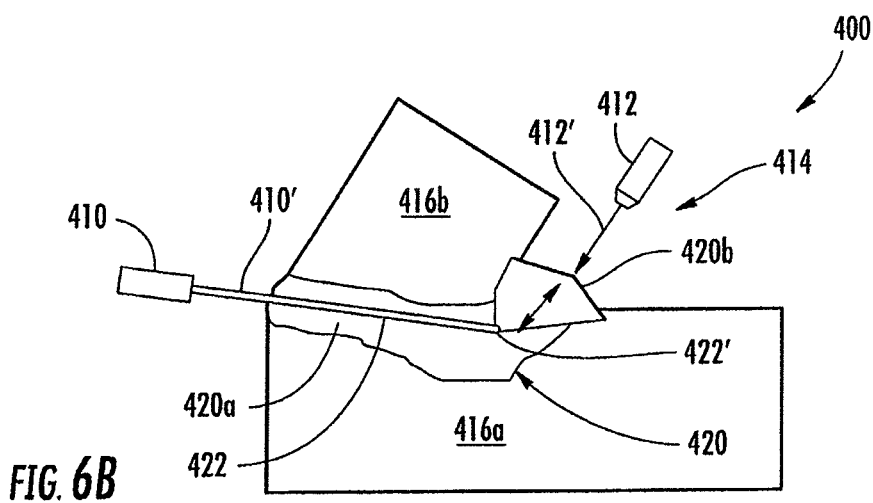
Figure 7A:
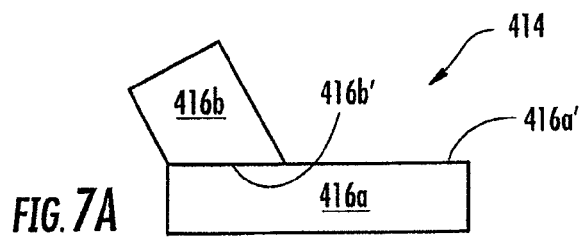
Figure 7B:
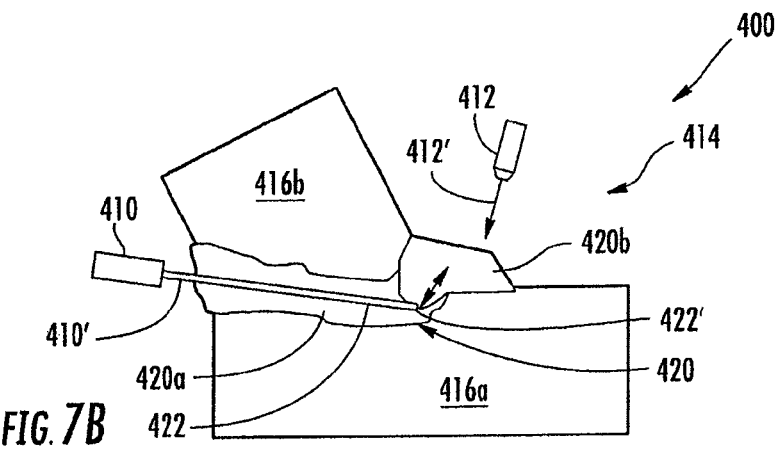
Figure 8:
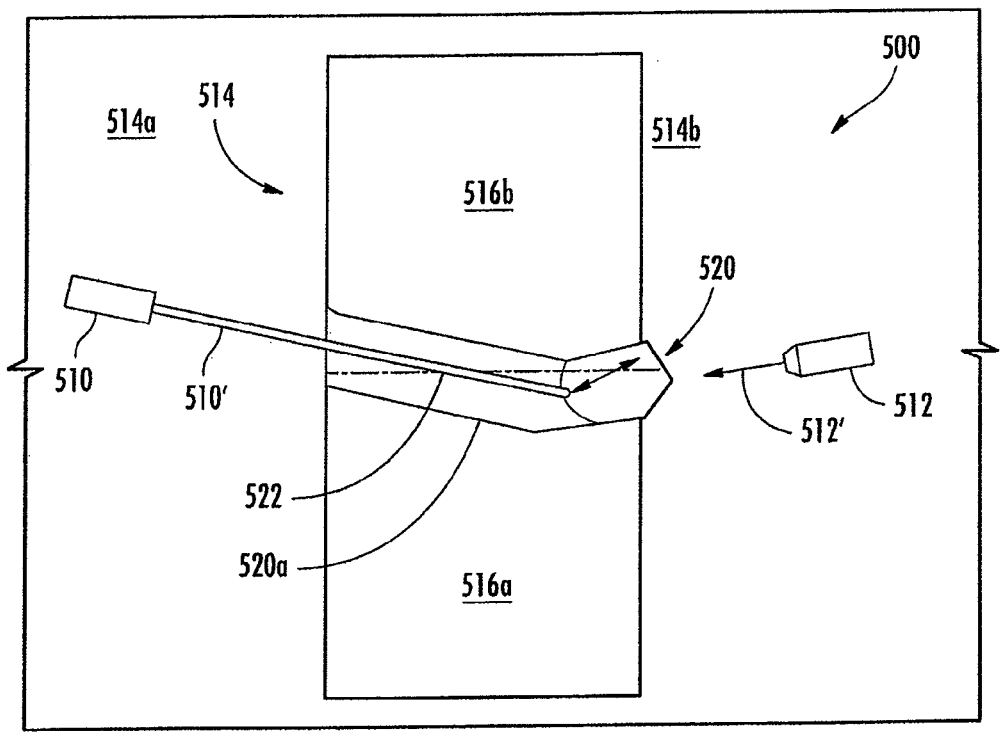
Figure 9A:
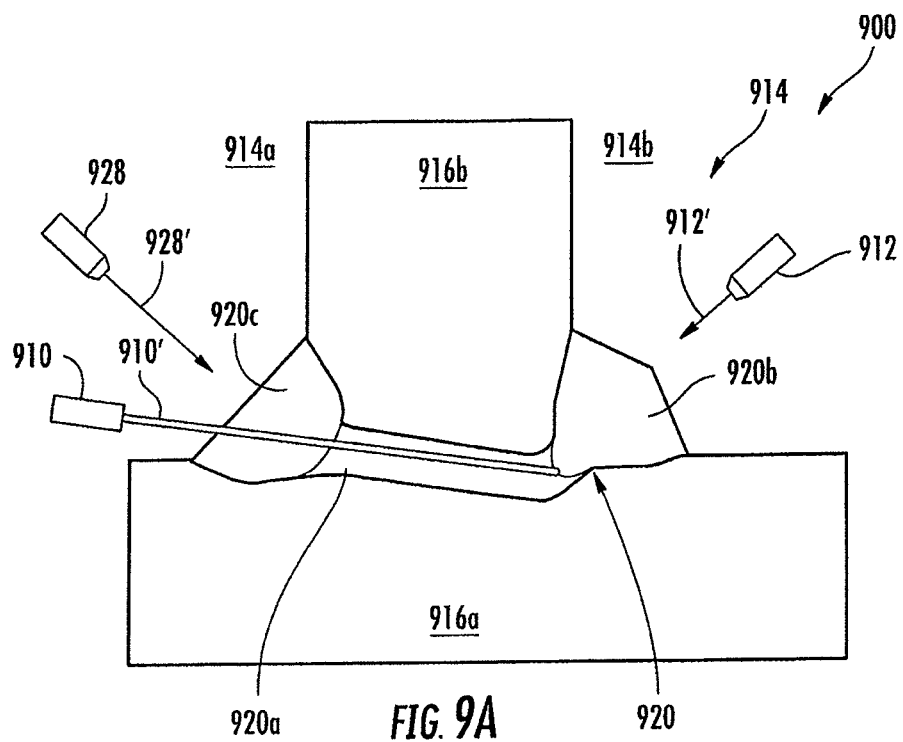
Figure 9B:
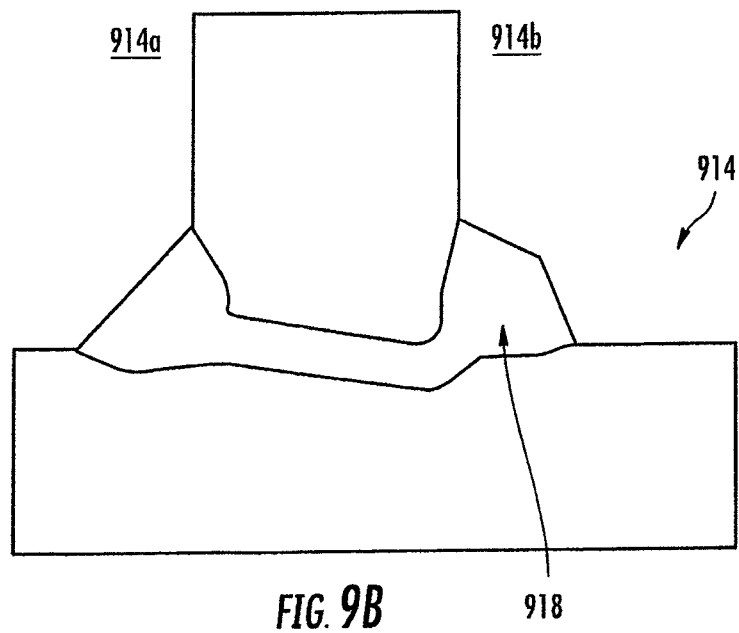
Figure 10A:
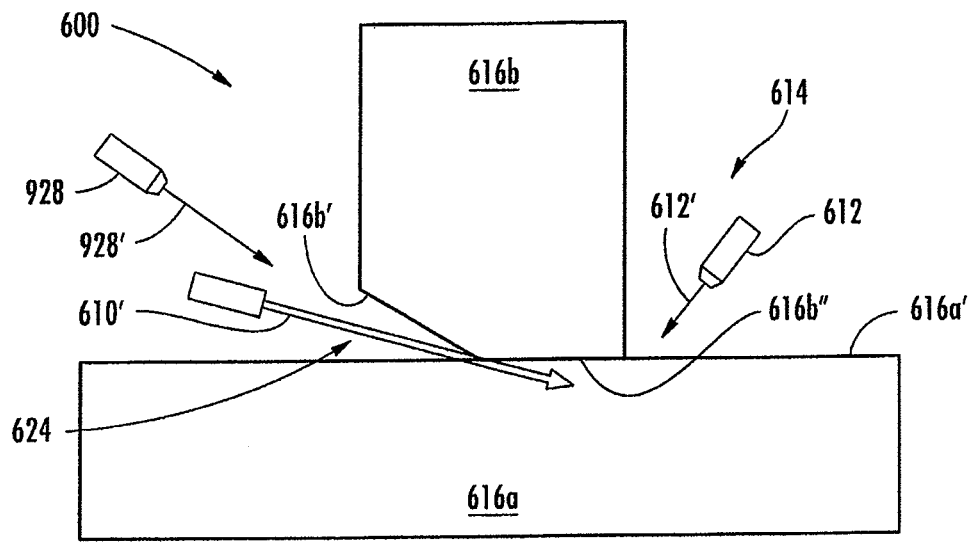
Figure 10B:
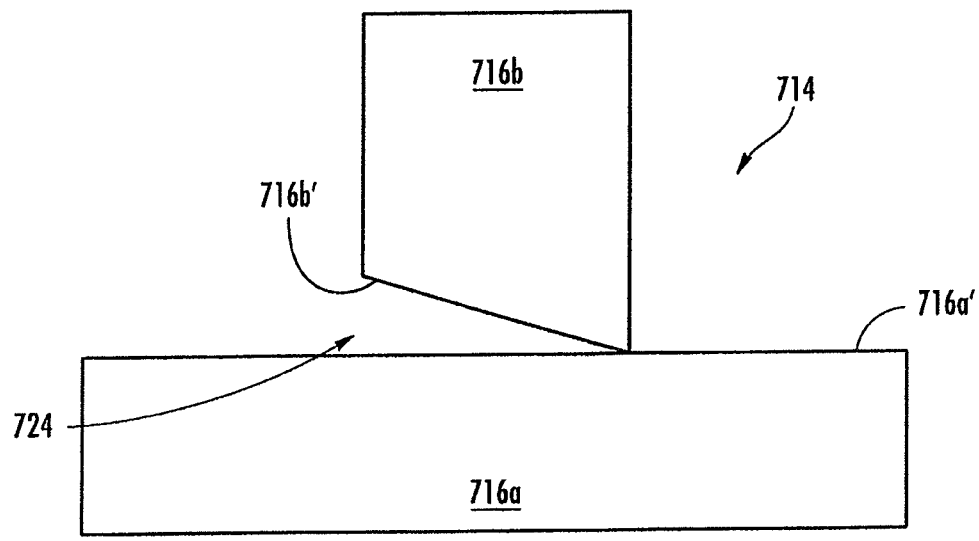
Figure 10C:
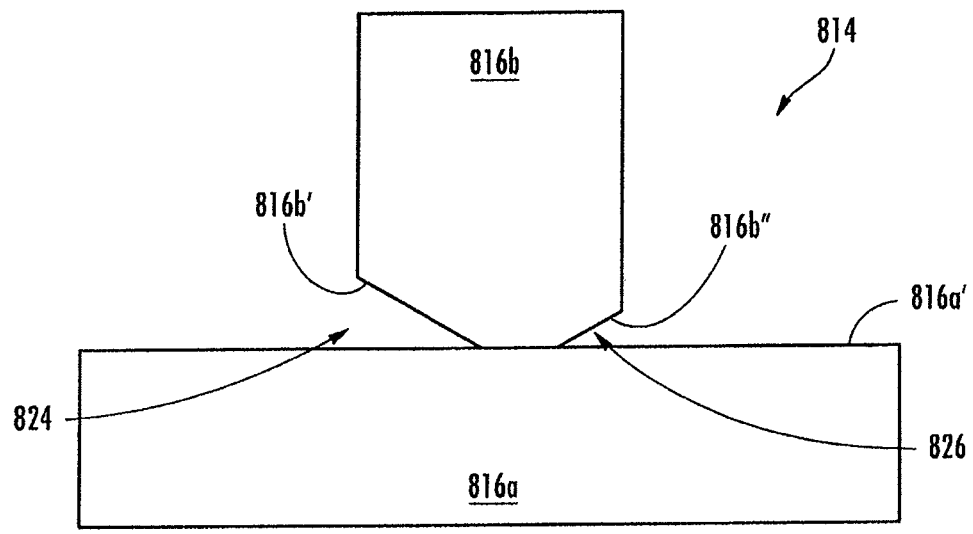
Figure 11A:
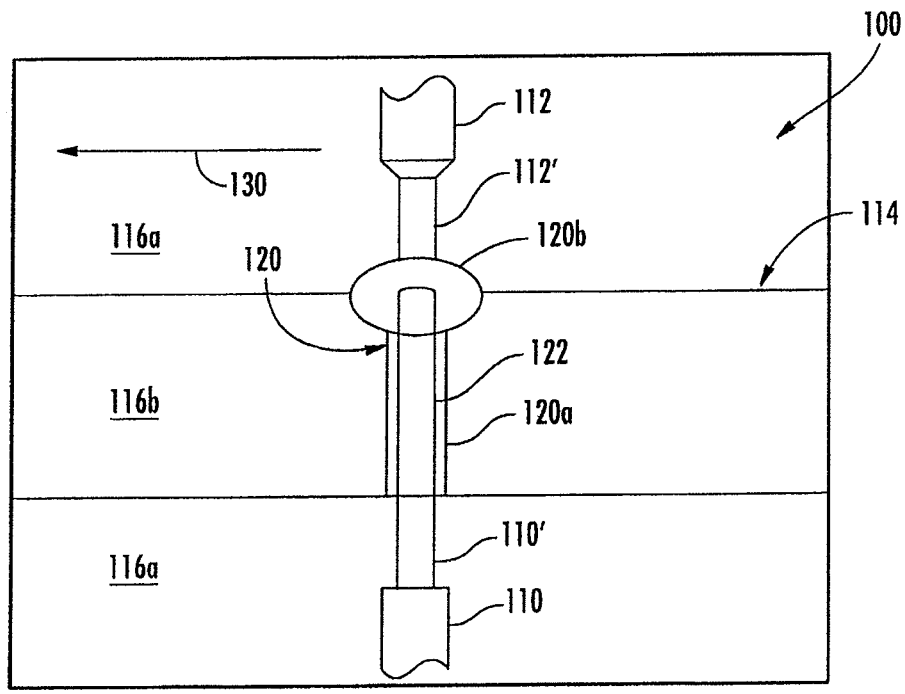
Figure 11B:
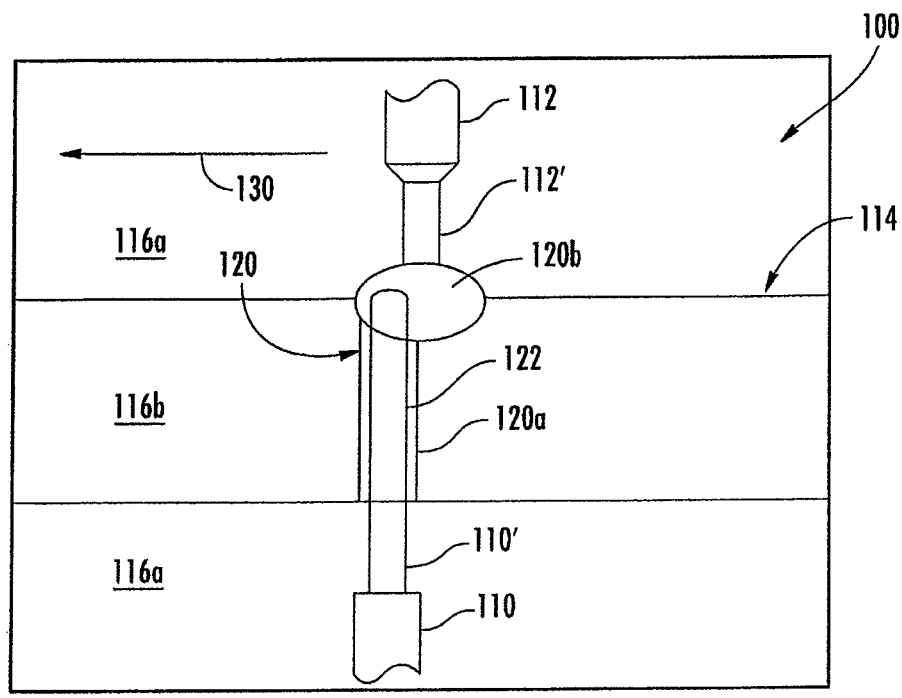
Figure 11C:
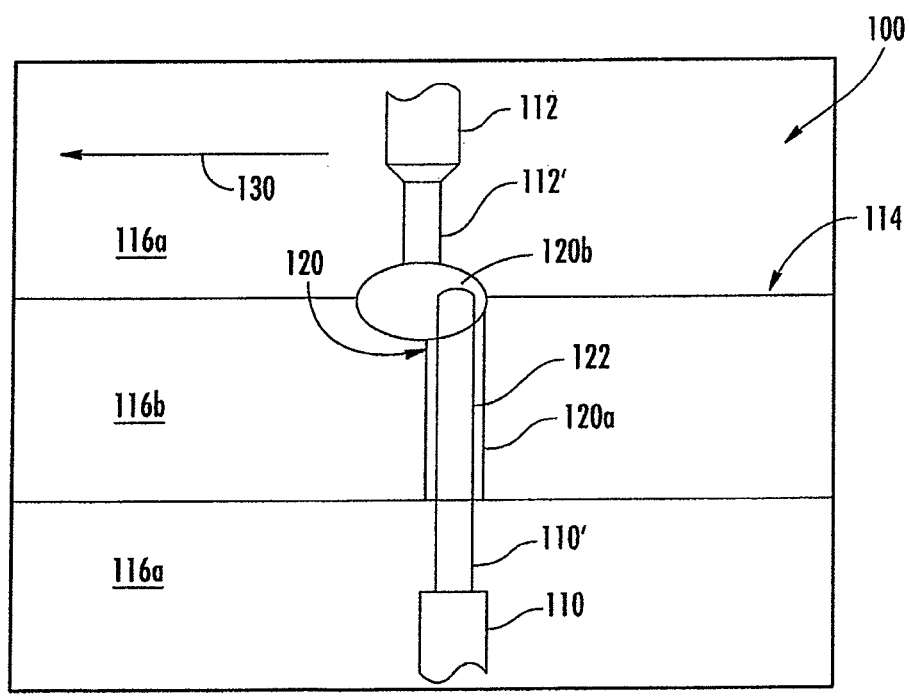
Figure 12:
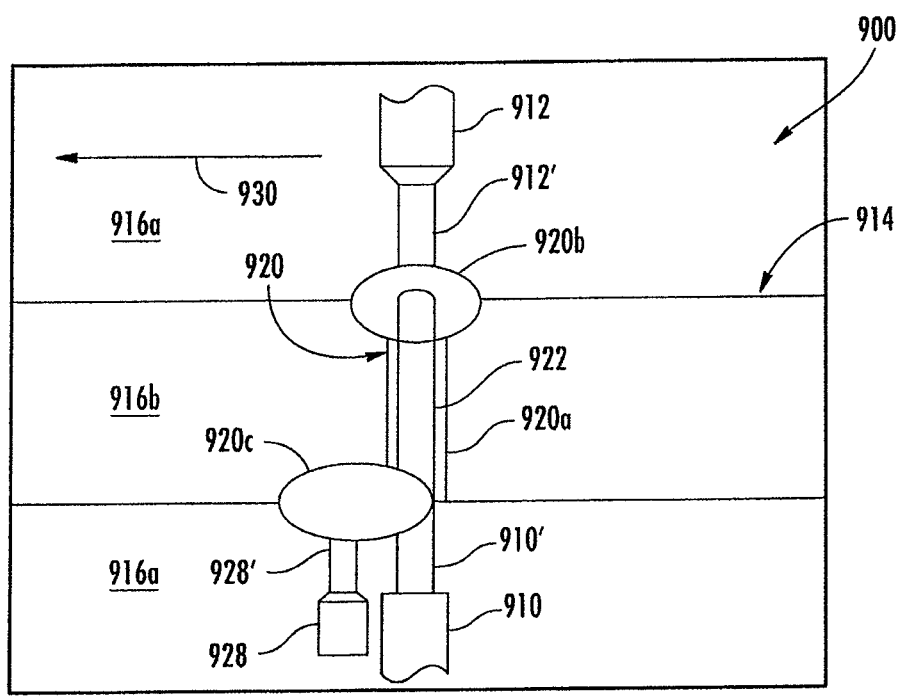
Figure 13:
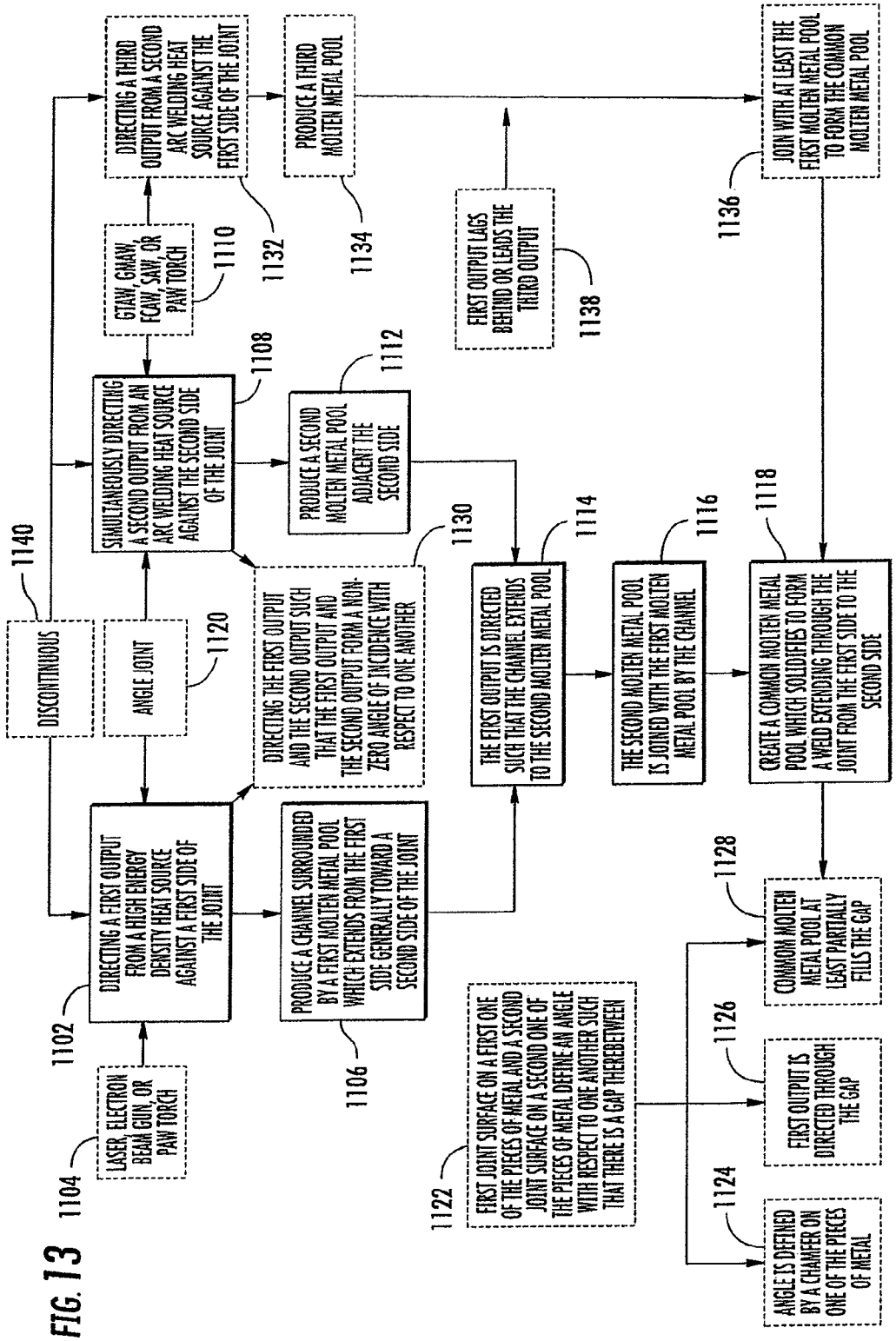
Figure 14:
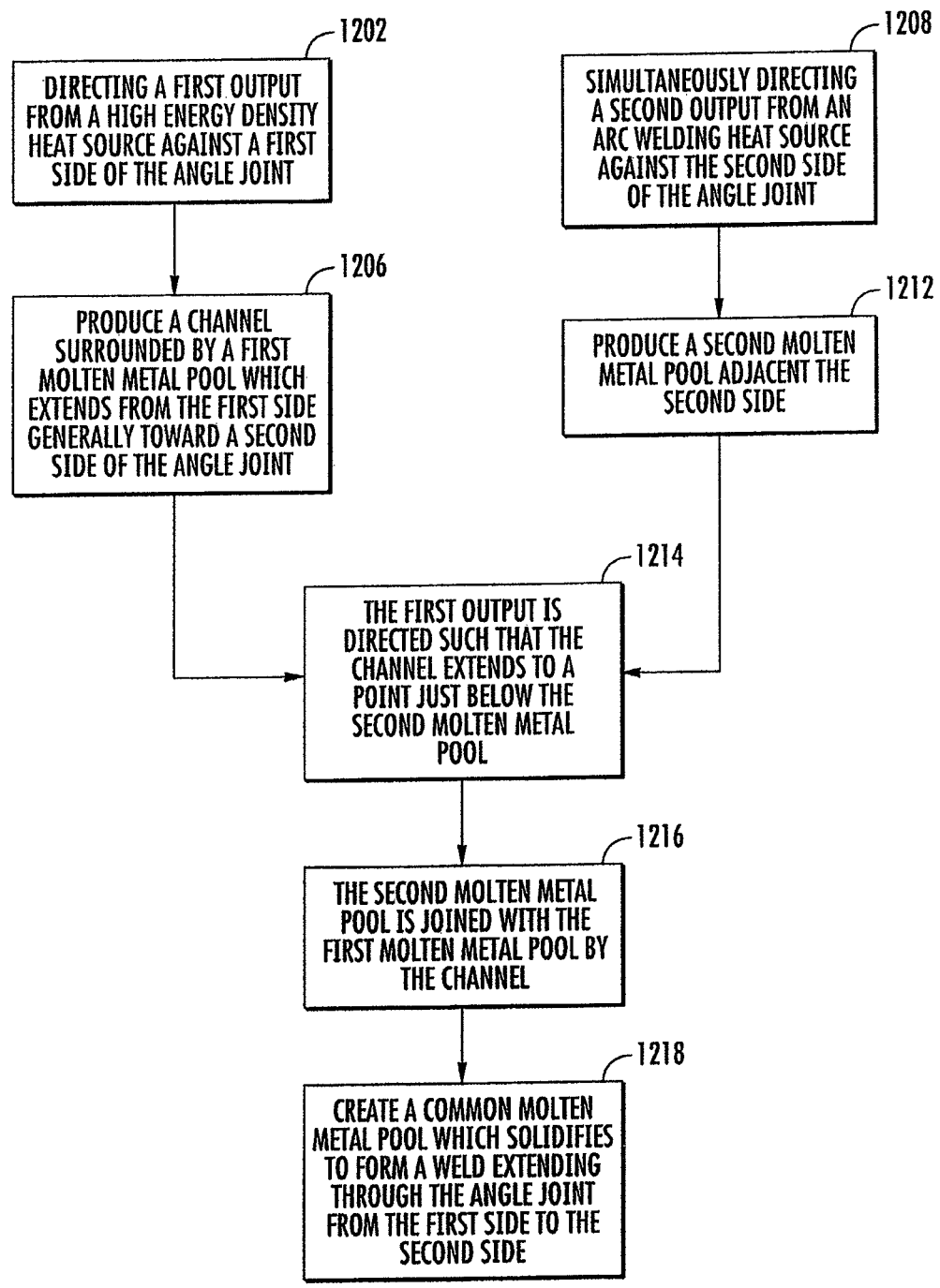

In the Drawings,

Sheets 1-13, Figures 1A-14, should be cancelled.

Signed and Sealed this
Fourth Day of August, 2015

Michelle K. Lee
*Director of the United States Patent and Trademark Office*